US012746366B2

(12) United States Patent
Appling et al.

(10) Patent No.: US 12,746,366 B2
(45) Date of Patent: Sep. 29, 2026

(54) ROTATIONAL AND DEFLECTABLE CATHETER CONTROL ASSEMBLY

(71) Applicant: EnTellect Medical Holdings, Louisville, KY (US)

(72) Inventors: Anthony Appling, Crestwood, KY (US); Ben Morris, Jeffersonville, IN (US); Chase Wooley, New Albany, IN (US)

(73) Assignee: EnTellect Medical Holdings

( * ) Notice: Subject to any disclaimer, the term of this patent is extended or adjusted under 35 U.S.C. 154(b) by 1043 days.

(21) Appl. No.: 17/950,165

(22) Filed: Sep. 22, 2022

(65) Prior Publication Data

US 2023/0086301 A1 Mar. 23, 2023

Related U.S. Application Data

(60) Provisional application No. 63/246,835, filed on Sep. 22, 2021.

(51) Int. Cl.
*A61M 25/01* (2006.01)
*A61B 1/005* (2006.01)
(Continued)

(52) U.S. Cl.
CPC .... *A61M 25/0147* (2013.01); *A61M 25/0158* (2013.01); *A61B 1/0052* (2013.01);
(Continued)

(58) Field of Classification Search
CPC .......... A61M 25/0097; A61M 25/0136; A61M 25/0105; A61M 1/772; A61M 39/223;
(Continued)

(56) References Cited

U.S. PATENT DOCUMENTS 4,750,477 A * 6/1988 Wardle .................. A61B 1/307
600/149
5,486,155 A * 1/1996 Muller ............... A61B 1/00135
600/137
(Continued)

FOREIGN PATENT DOCUMENTS

DE 19819432 A1 * 11/1999 ............ A61M 1/774
WO WO-2021071692 A1 * 4/2021 ......... A61B 18/1492

*Primary Examiner* — Emily L Schmidt
*Assistant Examiner* — Martin A Radomski
(74) *Attorney, Agent, or Firm* — Dickinson Wright PLLC

(57) ABSTRACT

A control assembly for a catheter includes a housing extending along an axis between a proximal and distal housing end to define a housing compartment. A control case is disposed within the housing compartment, and a catheter shaft extends from the control case to a distal tip. The working component of the catheter includes at least one channel component extending from a static portion disposed in fixed and stationary relationship relative to the control case to a dynamic portion extending along and rotatable about the axis simultaneously with the catheter shaft. A lumen interruption mechanism is disposed in the control case and extends from a proximal mechanism end disposed in communication with the static portion of the channel component to a distal mechanism end disposed in communication with the dynamic portion of the channel component to transition the channel component between the static and dynamic portions.

18 Claims, 18 Drawing Sheets

(51) Int. Cl.
*A61B 17/34* (2006.01)
*A61M 25/00* (2006.01)

(52) U.S. Cl.
CPC ...... *A61B 17/3462* (2013.01); *A61M 25/0097* (2013.01); *A61M 25/0105* (2013.01); *A61M 25/0136* (2013.01)

(58) Field of Classification Search
CPC ........ A61M 2039/229; A61M 25/0147; A61B 1/0052; A61B 17/3462
See application file for complete search history.

(56) References Cited

U.S. PATENT DOCUMENTS

| | | | | | |
|---|---|---|---|---|---|
| 5,810,718 | A * | 9/1998 | Akiba | G02B 23/2476 | 600/156 |
| 8,690,761 | B2 * | 4/2014 | Begemann | A61M 3/0283 | 600/116 |
| 11,116,942 | B2 | 9/2021 | Beeckler et al. | | |
| 2004/0181135 | A1 * | 9/2004 | Drysen | A61M 25/0136 | 600/374 |
| 2013/0184528 | A1 | 7/2013 | Onuki et al. | | |
| 2014/0012075 | A1 * | 1/2014 | Konstorum | A61B 1/0052 | 600/104 |
| 2014/0012194 | A1 * | 1/2014 | Terwiske | A61M 39/22 | 604/99.04 |
| 2014/0228800 | A1 * | 8/2014 | Rezac | A61M 25/0147 | 604/95.04 |
| 2014/0276393 | A1 * | 9/2014 | Park | A61M 25/0097 | 604/95.01 |
| 2016/0074624 | A1 * | 3/2016 | Morris | A61M 25/0136 | 604/95.04 |
| 2016/0074625 | A1 * | 3/2016 | Furnish | A61M 25/0133 | 604/95.04 |
| 2018/0264231 | A1 * | 9/2018 | Scheibe | A61M 25/0133 | |
| 2020/0359879 | A1 * | 11/2020 | Cahill | A61B 1/05 | |
| 2021/0235973 | A1 * | 8/2021 | Gray | A61B 1/00042 | |
| 2021/0338984 | A1 * | 11/2021 | Booker | A61M 25/0097 | |

* cited by examiner

ROTATIONAL AND DEFLECTABLE CATHETER CONTROL ASSEMBLY

CROSS-REFERENCE TO RELATED APPLICATION

The subject application claims the benefit of U.S. Provisional Application Ser. No. 63/246,835 filed on Sep. 22, 2021, the entire disclosure of which is incorporated herein by reference.

TECHNICAL FIELD

The present disclosure relates to a control assembly for a medical interventional device, such as catheter. More particularly, the present disclosure relates to a control assembly capable of providing both rotation and deflection of a distal tip of a catheter in response to movement of at least one actuator dial by a user.

BACKGROUND OF THE INVENTION

A catheter is a medical instrument for use in accessing an interior of a patient's body with a distal tip during a medical procedure. The catheter can include at least one working component, such as a fluid channel, a working channel, and/or an electronics cable, which extend along the catheter and terminate at or adjacent the distal tip. Catheters typically have a control handle which is configured to allow a user to control a position of the distal tip during the procedure, such as via rotation of a knob on the control handle to effectuate rotation of the catheter and the distal tip about an axis. However, the working components which pass through the catheter shaft are prone to winding, overlapping, occlusion or other damage during their simultaneous rotation with the catheter shaft. Torsional stresses and crossing of the working components caused during rotation of the catheter shaft can damage or impair the function of the catheter device. For example, the fluid channel is utilized to deliver fluids and the working channel is utilized to deliver an instrument to the distal tip of the catheter during the medical procedure. However, kinking, crossing or other occlusion of these channel components can prevent the related fluids or instrument from reaching the distal tip during the medical procedure, and thus resulting in an ineffective catheter that fails during the medical procedure. Additionally, knotting or worse yet facture of the electronics cable can lead to full loss of function of the electronics. Thus, there remains a need for improvements to such catheter control assemblies in which the catheter shaft is rotatable about the axis during the medical procedure by a user and includes at least one working component.

SUMMARY OF THE INVENTION

A control assembly for a catheter having at least one working component includes a housing extending along an axis between a proximal housing end and a distal housing end to define a housing compartment extending therebetween. A control case is disposed within the housing compartment adjacent the proximal housing end. A catheter shaft extends within the housing compartment from the control case to a distal tip disposed adjacent the distal housing end. The catheter shaft is rotatable about the axis during operation of the control assembly to effectuate rotation of the distal tip. At least one working component of the catheter includes at least one channel component extending from a static portion disposed adjacent the proximal housing end in coupled and generally stationary relationship relative to the control case to a dynamic portion extending along and rotatable about the axis simultaneously with the catheter shaft. A lumen interruption mechanism is disposed in the control case and extends from a proximal mechanism end disposed in communication with the static portion of the at least one channel component to a distal mechanism end disposed in communication with the dynamic portion of said at least one channel component. As will be more fully explained in the following detailed description, the lumen interruption mechanism transitions the at least one channel component from the static portion to the dynamic portion as the at least one channel component translates through the housing compartment and is dynamically rotated about the axis simultaneously with the catheter shaft to maintain the integrity of the dynamic portion of the at least one channel component, and avoid damage such as via kinking, occlusion, or the like during use of the control assembly in a medical procedure.

BRIEF DESCRIPTION OF THE DRAWINGS

Other aspects of the present disclosure will be readily appreciated, as the same becomes better understood by reference to the following detailed description when considered in connection with the accompanying drawings wherein.

DETAILED DESCRIPTION OF THE EXEMPLARY EMBODIMENTS

In the following description, details are set forth to provide an understanding of the present disclosure. In some instances, certain systems, structures and techniques have not been described or shown in detail in order not to obscure the disclosure.

Figure 1:
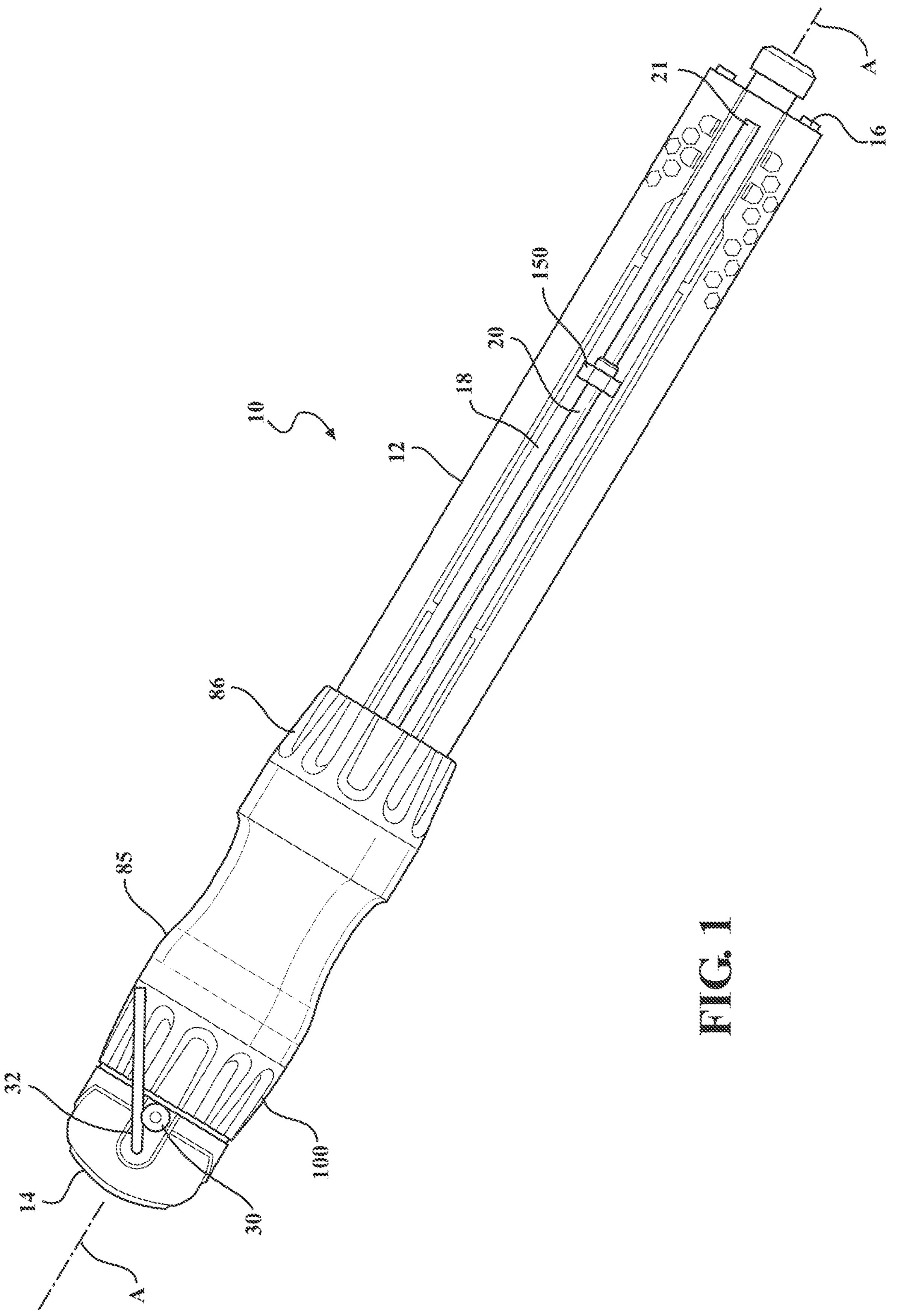
FIG. 1 is a perspective view of a control assembly including a housing extending from a proximal housing end to a distal housing end along an axis A and a handle portion disposed adjacent the proximal housing end and axially translatable along the housing towards the distal housing end.

Referring to the Figures, wherein like numerals indicate corresponding parts throughout the several views, a control assembly 10 for a medical interventional device, such as a catheter, is generally shown. While the subject control assembly 10 is described herein for use with a catheter, it should be appreciated that the control assembly 10 could be used in association with other medical interventional devices without departing from the scope of the subject disclosure. As best illustrated in FIGS. 1 and 1A, the catheter control assembly 10 includes a housing 12 which extends in a longitudinal direction along an axis A between a proximal housing end 14 and a distal housing end 16 to define a housing compartment 18 for receiving the catheter, along with at least one of its associated working components, namely a working channel component 22, a fluid channel component 24, and/or an electronics cable 26.

Figure 1A:
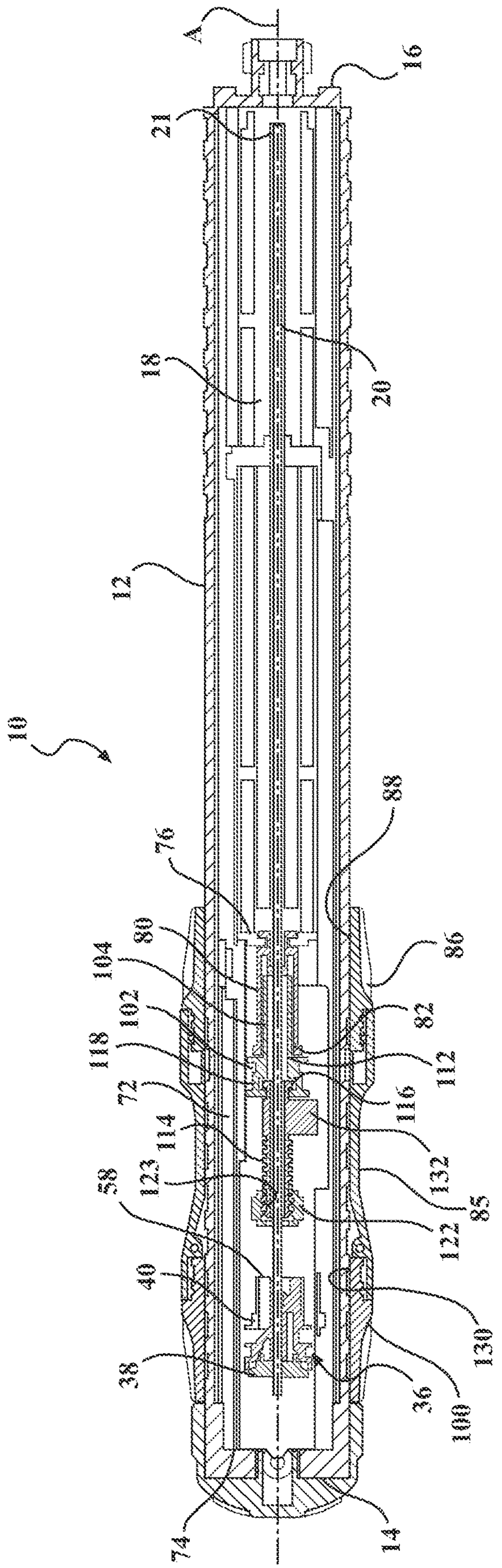
FIG. 1A is a cross-sectional view of the control assembly illustrating a control case disposed within the housing adjacent the proximal housing end and a catheter shaft extending from a distal case end of the control case to a distal tip disposed adjacent the distal housing end.
Figure 2:
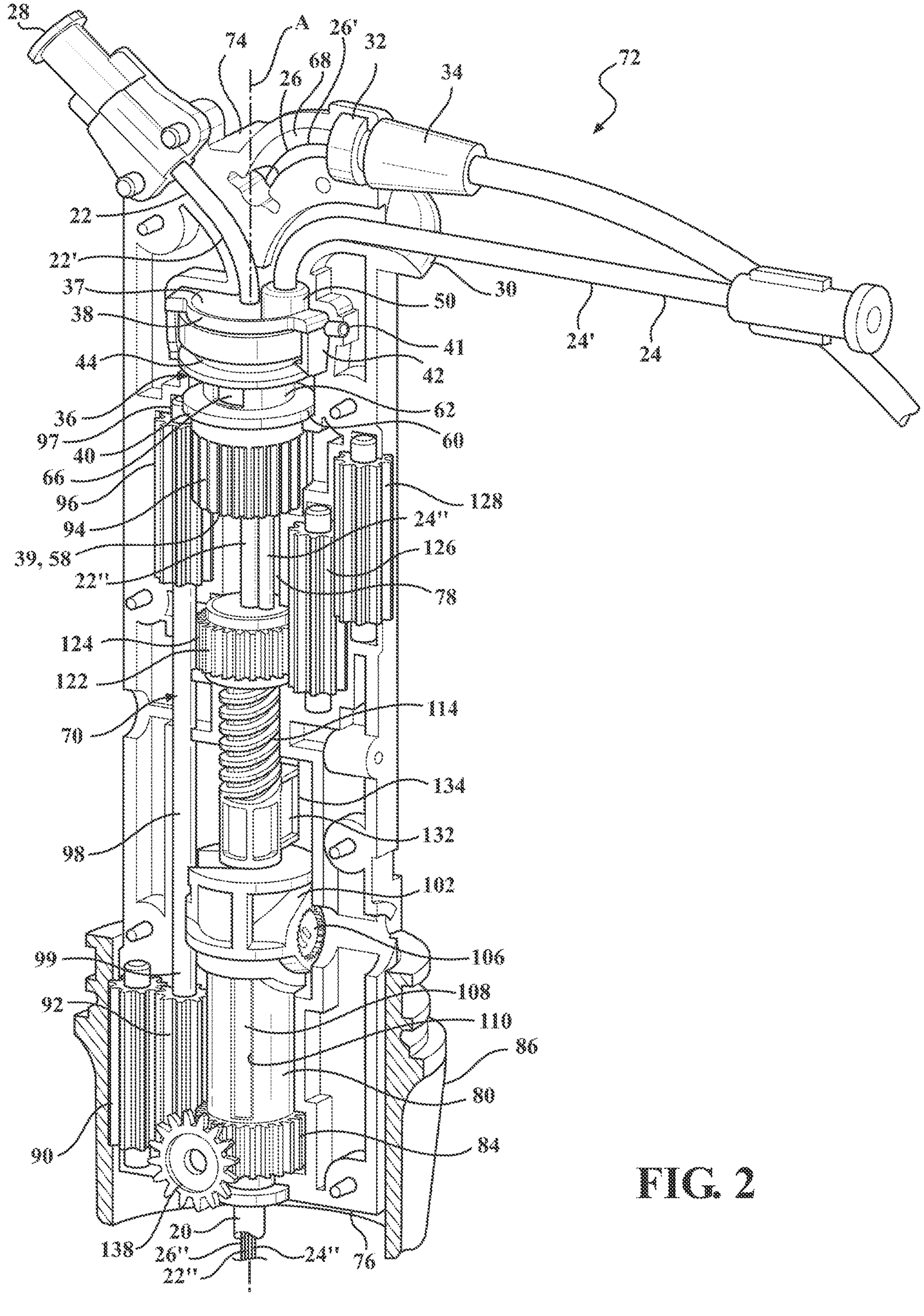
FIG. 2 is a perspective view of the control case illustrating a lumen interruption mechanism disposed adjacent a proximal case end, a center gear disposed adjacent the distal case end, a synchronous rotation mechanism operably coupling a union reservoir hub of the lumen interruption mechanism and the center gear for establishing simultaneous and synchronous rotation of these components, and a cable take-up assembly.
Figure 19:
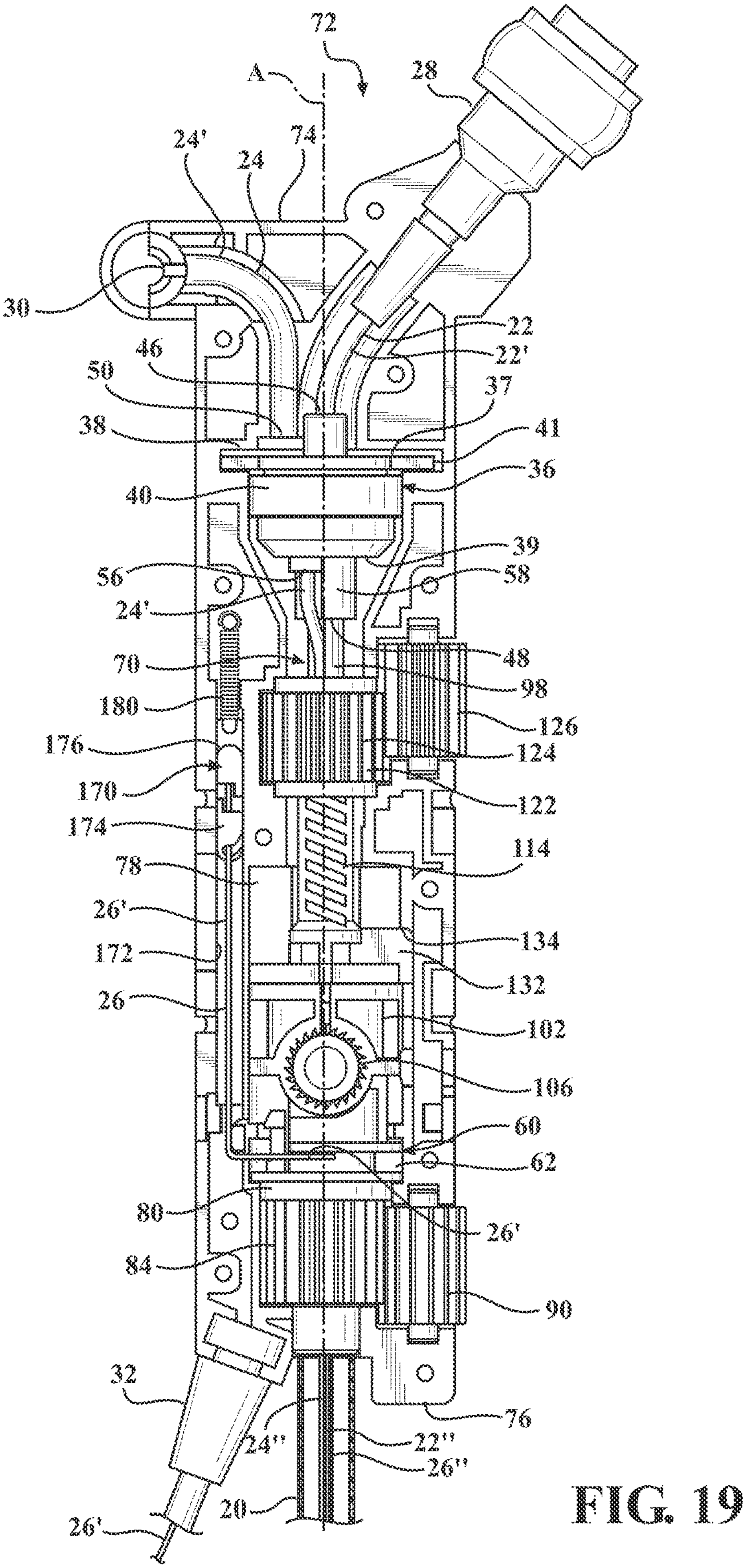
FIG. 19 is a cross-sectional view of the control case illustrating alternative embodiments of the synchronous rotation mechanism and the cable take-up assembly.

More specifically, and as further illustrated in FIGS. 1A, a control case 72 is disposed within the housing compartment 18 adjacent the proximal housing end 14, and a catheter shaft 20 extends within the housing compartment 18 from the control case 72 and extending through and beyond the housing compartment to a distal tip 21 disposed adjacent and exterior to the distal housing end 16. The working channel component 22 and the fluid channel component 24 of the catheter extend from respective static portions 22', 24' disposed adjacent the proximal housing end 14 in coupled and generally stationary relationship relative to the control case 72 and the housing 12 during operation of the control assembly 10. For example, as best illustrated in FIGS. 2 and 19, a proximal case end 74 of the control case 72 includes a working channel port 28 and a fluid channel port 30, each for receiving respective static portions 22', 24' of the working channel and fluid channel components 22, 24 from an environment of the control assembly 10. The electronics cable component 26 also extends from a static portion 26' disposed in coupled and generally stationary relationship relative to the control case 72 and the housing 12 during operation of the control assembly 10. For example, as also illustrated in FIG. 2, the proximal case end 74 of the control case 72 can additionally include an electronics port 32 including a strain relief sheath 34 for receiving the static portion 26' of the electronics cable 26 from the environment of the control assembly 10. However, as illustrated in FIG. 19, the electronics port 32 can also be disposed adjacent the distal case end 76 of the control case 72 such that the static portion 26' of the electronics cable 26 enters the control case 72 and is coupled generally stationary relative to the distal case end 76 without departing from the scope of the subject disclosure.

Each of the static portions 22', 24', 26' of the working channel component 22, the fluid channel component 24 and the electronics cable 26 communicate with respective dynamic portions 22", 24", 26" that extend along and are rotatable about the axis A simultaneously with the catheter shaft 20. In other words, the catheter shaft 20 houses a dynamic portion 22" of the working channel component 22, a dynamic portion 24" of the fluid channel component 24, and a dynamic portion 26" of the electronics cable 26 that pass through the catheter shaft 20 and break out at one or more locations adjacent or at the distal tip 21 of the catheter shaft 20.

As noted previously, for a catheter shaft 20 that rotates during operation of the control assembly 10 in response to control by a user, it is problematic for the dynamic portions 22", 24", 26" of the working channel, fluid channel and electronics cable components 22, 24, 26 (i.e., those portions of the working channel 22, fluid channel 24 and electronics cable 26 passing through the compartment 18 of the housing 12 and along the catheter shaft 20) to wind or overlap during rotation of the catheter shaft 20. Torsional stresses and the crossing of the dynamic portions of these working components 22, 24, 26 during rotation can lead to damage or impair the function of the catheter. Accordingly, the control assembly 10 includes a lumen interruption mechanism 36 disposed adjacent the proximal housing end 14 of the control assembly 10 for transitioning the working components 22, 24, 26 from their static portions 22', 24', 26' as they enter the control assembly 10 to their dynamic portions 22", 24", 26" as they translate through the compartment 18 of the housing 12 and are dynamically rotated about the axis A simultaneously with the catheter shaft 20 to achieve rotational control of the distal tip 18 during a procedure.

Figure 4:
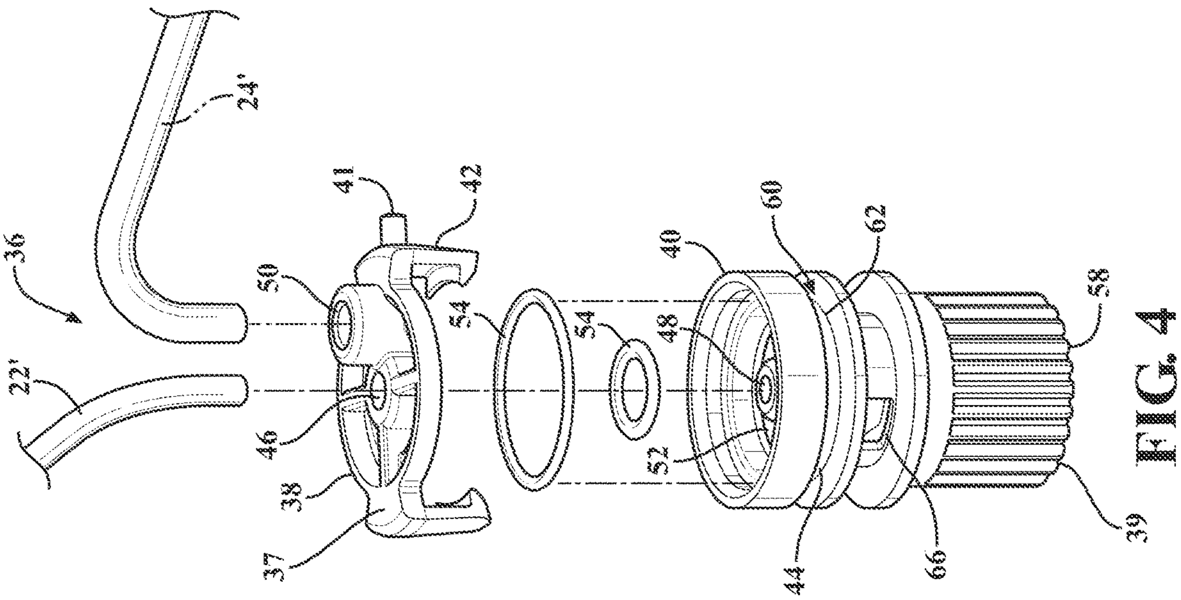
FIG. 4 is an exploded perspective view of the lumen interruption mechanism.
Figure 3:
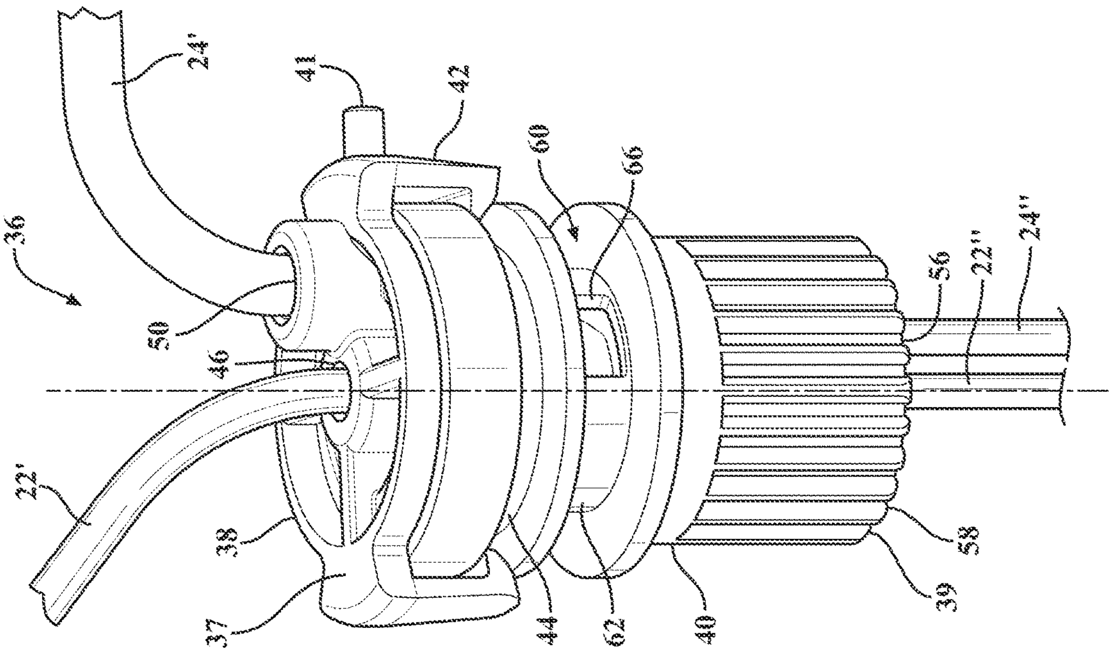
FIG. 3 is a perspective view of the lumen interruption mechanism illustrating the union reservoir hub rotatably coupled to a static, union reservoir cap and including the cable take-up assembly.
Figure 5:
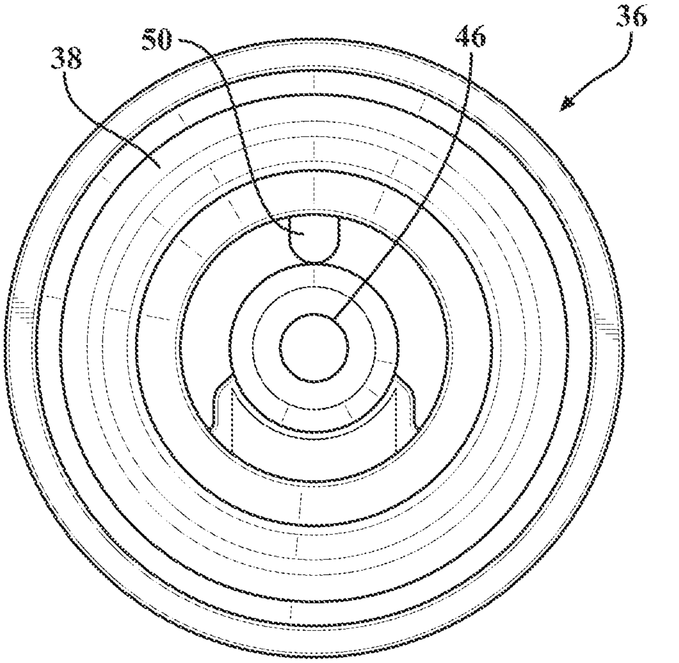
FIG. 5 is a top view of the lumen interruption mechanism.
Figure 6:
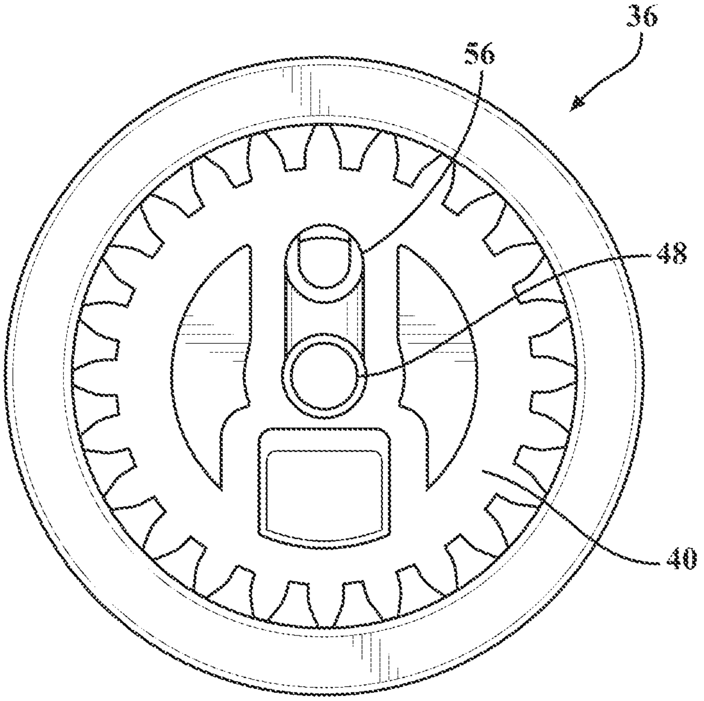
FIG. 6 is a bottom view of the lumen interruption mechanism.

As best illustrated in FIGS. 3-4, 7-8 and 19, the lumen interruption mechanism 36 is disposed in the control case 72 adjacent the proximal case end 74 and extends from a proximal mechanism end 37 disposed in communication with the static portions 22', 24' of the working channel component 22 and the fluid channel component 24 to a distal mechanism end 39 disposed in communication with the dynamic portions 22", 24" of the working channel component 22 and the fluid channel component 24 for transitioning the working channel and fluid channel components 22, 24 from their static to dynamic portions. The lumen interruption mechanism 36 includes a union reservoir cap 38 that is static (i.e., disposed in a generally fixed/non-movable condition) relative to the housing 12 of the control assembly 10 and a union reservoir hub 40 that is rotatably coupled to the union reservoir cap 38 and dynamically free to fully rotate about the axis A and relative to the union reservoir cap 38 within the control handle 10 and the control case 72. As best illustrated in FIGS. 3 and 19, the union reservoir cap 38 includes a post 41 that mates with a corresponding portion of the control handle 38 to keep the union reservoir cap 38 from rotating about the axis A and maintain the union reservoir cap 38 in its static position. As also illustrated in FIGS. 3 and 4, in a preferred arrangement, the union reservoir cap 38 includes a pair of legs 42 that extend along an outer portion of the union reservoir hub 40 and terminate in a rotational channel 44 defined by the union reservoir hub 40 for rotatably coupling these two components together. However, other means of fixing the union reservoir cap 36 and establishing the rotatable coupling of the union reservoir cap and hub 36, 38 could be utilized without departing from the scope of the subject disclosure.

Figure 8:
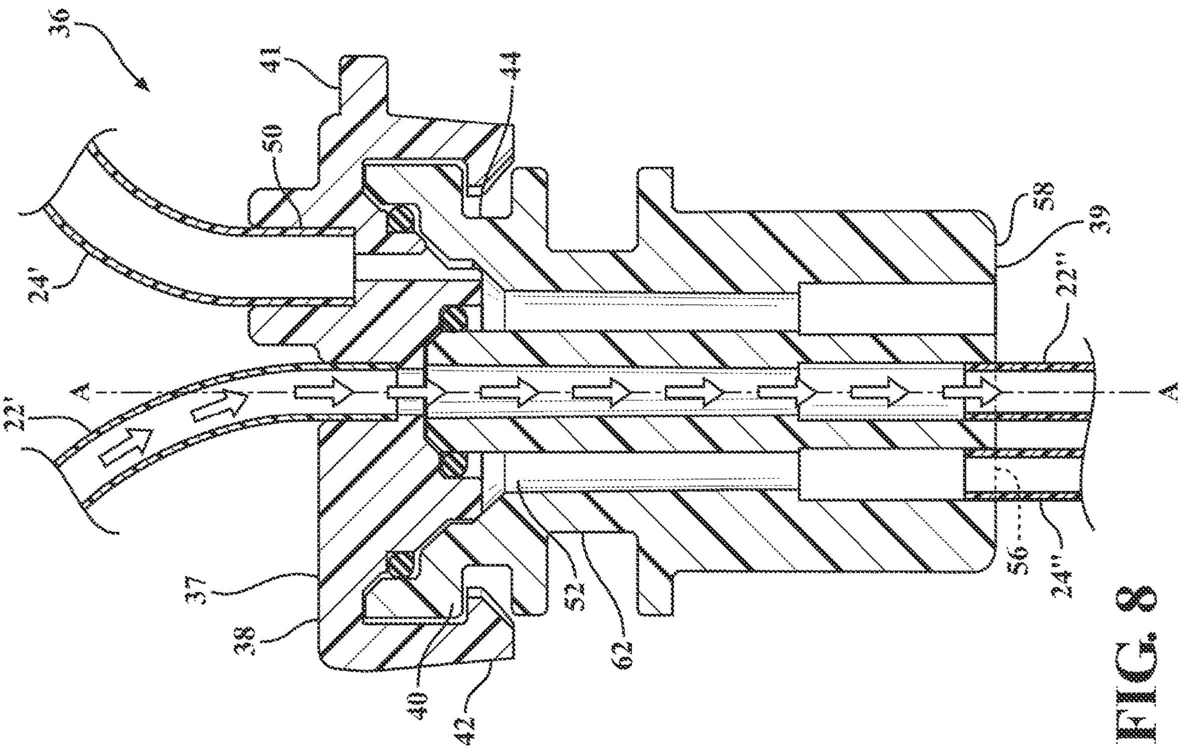
FIG. 8 is a cross-sectional view of the lumen interruption mechanism illustrating a fluid tight working channel extending axially through the union reservoir cap and hub between a central cap orifice and a central hub orifice.
Figure 7:
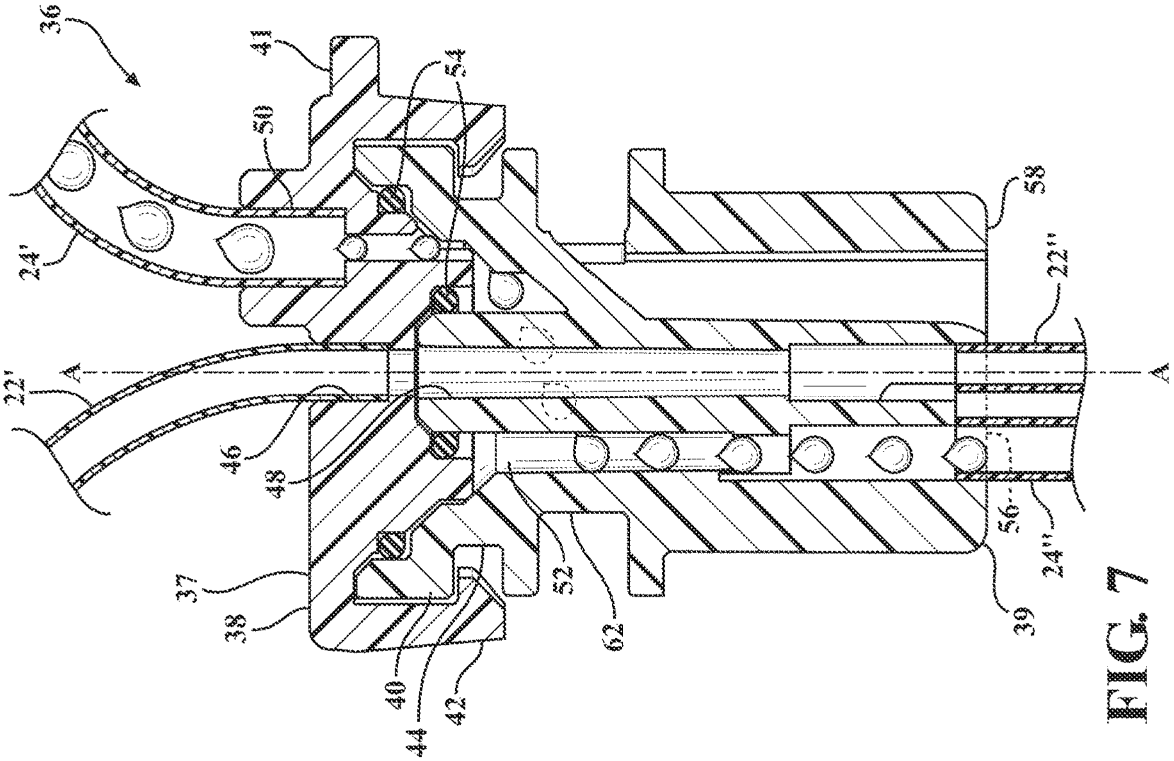
FIG. 7 is a cross-sectional view of the lumen interruption mechanism illustrating a sealed fluid communication path extending through the union reservoir cap and hub sequentially via a cap fluid inlet, a fluid reservoir and a cap fluid outlet.

As best illustrated in FIGS. 4-8 and 19, the union reservoir cap 38 defines a central cap inlet 46 and the union reservoir hub 40 defines a central hub outlet 48. Each of the central cap inlet 46 and central hub outlet 46, 48 extend through their respective components in aligned relationship with the axis A to dispose the inlet and outlet 46, 48 in aligned, fluid communication with one another when the union reservoir cap and hub 38, 40 are rotatably coupled together. With reference to FIG. 8, the aligned central cap and hub inlet and outlet 46, 48 define a fluid tight working channel, with a uniform ID that extends through the lumen interruption mechanism 36. The union reservoir cap 38 also defines a cap fluid inlet 50 disposed in radially offset relationship with the axis A, extending in generally parallel relationship with the central cap inlet 46. The union reservoir hub 40 defines a fluid reservoir 52 extending circumferentially about the central hub outlet 48 and disposed adjacent the central reservoir cap 38 in fluid communication with the cap fluid inlet 50. As best illustrated in FIGS. 4 and 7-8, at least one sealing device 54, such as an o-ring, gasket, gland or the like, is disposed between the union reservoir cap and hub 38, 40 to seal the fluid reservoir 52. A cap fluid outlet 56 extends in radially spaced and generally parallel relationship with the axis A from the fluid reservoir 52 to a bottom end 58 of the union reservoir hub 40. Thus, as best illustrated in FIG. 7, a fluid communication path is established through the rotatably coupled union reservoir cap and hub 38, 40 sequentially via the cap fluid inlet 50, the fluid reservoir 52, and the cap fluid outlet 54, with fluid communication maintained between the cap fluid inlet and outlets 50, 54 even during rotation of the union reservoir hub 40 relative to the union reservoir cap 38 via the circumferntially-shaped fluid reservoir 52.

As best illustrated in FIGS. 3, 7-8 and 19, the dynamic portion 22" of the working channel component 22 extending from at or adjacent the distal end 21 of the catheter shaft 20 terminates at the bottom end 58 of the union reservoir hub 40 and is coupled to the central hub outlet 48. Similarly, the dynamic portion 24" of the fluid channel component 24 extending from at or adjacent the distal tip 21 of the catheter shaft 20 terminates at the bottom end 58 of the union reservoir hub 40 and is coupled to the hub fluid outlet 56. As further illustrated in FIGS. 2-3 and 19, the static portion 22' of the working channel component 22 extends from the working channel port 28, terminates at the union reservoir cap 38 and is coupled with the central cap inlet 46. Similarly, the static portion 24' of the fluid channel component 24 extends from the fluid channel port 30, terminates at the union reservoir cap 38 and is coupled to the cap fluid inlet 50.

In operation, and as will be explained in more detail below, rotation of the catheter shaft 20 to effectuate rotational movement of the distal tip 21, such as via rotation of a rotation control knob 86 on the control assembly 10 by a user, simultaneously and synchronously drives rotation of the union reservoir hub 40 relative to the union reservoir cap 38. As a result, the dynamic portions 22", 24" of the working and fluid channel components 22, 24 which each extend from the union reservoir hub 40 to the distal tip 21 of the catheter shaft 20 rotate simultaneously and synchronously with one another and the catheter shaft 20, while the static portions 22', 24' of the working and fluid channel components 22, 24 which extend from the union reservoir cap 38 to their respective ports 28, 30 remain in a static condition (notwithstanding rotational movement of the catheter shaft 20). Thus, as illustrated in FIG. 8, the lumen interruption mechanism 36 advantageously provides for a continuous ID working channel 22 that is static on the proximal mechanism end 37 of the lumen interruption mechanism 36 and torsionally dynamic on the distal mechanism end 39 of the lumen interruption mechanism 36, while remaining fluid tight. The collective working channel, resulting from the combination of the static portion of the working channel 22', the aligned central cup and hub inlet and outlet 46, 48, as well as the dynamic portion of the working channel 22", also remains centrally aligned on the axis A even during rotation of the catheter shaft 20. Furthermore, as illustrated in FIG. 7, the lumen interruption mechanism 36 allows for the passage of fluid therethrough from the cap fluid inlet 50 to the cap fluid outlet 56 through a secondary off-axis fluid communication path that is independent of the central, aligned and collective working channel extending along the axis A. In this way, static inputs to the lumen interruption mechanism 36 are not adversely affected by rotational movement of the catheter shaft 20 and kinking/occlusion/damage of the dynamic portions 22", 24" of the working channel components extending from the lumen interruption mechanism 36 to the distal tip 21 of the catheter shaft 20 is avoided. The dynamic portion of the working channel 22" and the dynamic portion of the fluid channel 24" remain in their same relative positions to one another even while the catheter shaft 20 is being rotated about the axis A to effectuate rotation of the distal tip 21. Thus, these working components 22, 24 do not wind or overlap when the catheter shaft 20 is rotating, improving the functionality of the control assembly 10 relative to prior art devices.

As previously mentioned, rotation of the catheter shaft 20 to effectuate rotational movement of the distal tip 21 simultaneously and synchronously drives rotation of the union reservoir hub 40 relative to the union reservoir cap 38. Synchronicity of these dynamic rotating mechanisms prevents winding and kinking of the various dynamic portions of the working components emanating from the union reservoir hub 40. By all elements rotating as "one single body" relative to the remaining components that make up the control assembly 10, winding damage within the control assembly 10 is negated. As will be described in more detail below with reference to FIGS. 1A, 2 and 19, this relationship is accomplished through the use of a synchronous rotation mechanism 70.

As best illustrated in FIGS. 1A, 2 and 19, the control case 72 extends from the proximal case end 74 to a distal case end 76 to define a control compartment 78 extending therebetween. The lumen interruption mechanism 36 is preferably disposed in the control compartment 78 adjacent the proximal case end 74. The control case 72 includes a center gear 80 disposed in the control compartment 78 adjacent the distal case end 76 in rotatably aligned relationship with the central axis A. As best illustrated in FIGS. 1A, 2 and 19, the catheter shaft 20 is secured or coupled to the center gear 80 for rotation therewith (as will be described in more detail below), and the center gear 80 defines a center gear passageway 82 extending along the axis A for allowing the dynamic portions of the working channel 22, fluid channel 24 and electronic cable 26 which extend from the catheter shaft 20 to pass through the center gear passageway 82, along the control compartment 78 and into their coupled positions with the union reservoir hub 40.

The center gear 80 defines a set of center gear teeth 84 extending radially outwardly from the center gear 80 in circumferentially aligned relationship with the central axis A. A handle portion 85 surrounds the control case 72 and includes the rotation control knob 86 rotatably disposed about the distal case end 76 of the control case 72. The rotation control knob 86 includes a set of rotation knob gear teeth 88 circumferentially arranged along an inner diameter of the rotation control knob 86. The rotation control knob 86 is oriented on the control case 72 such that its axis of rotation remains constant relative to the control assembly 10 and its axial position also remains constant. At least one spur gear 90, 92 is disposed between the rotation control knob 86 and the center gear 80 for disposing the rotation control knob 86 in operably coupled relationship with the set of center gear teeth 84 for driving rotation of the center gear 80 and the catheter shaft 20 in response to rotation of the rotation control knob 86 by a user.

Figure 23:
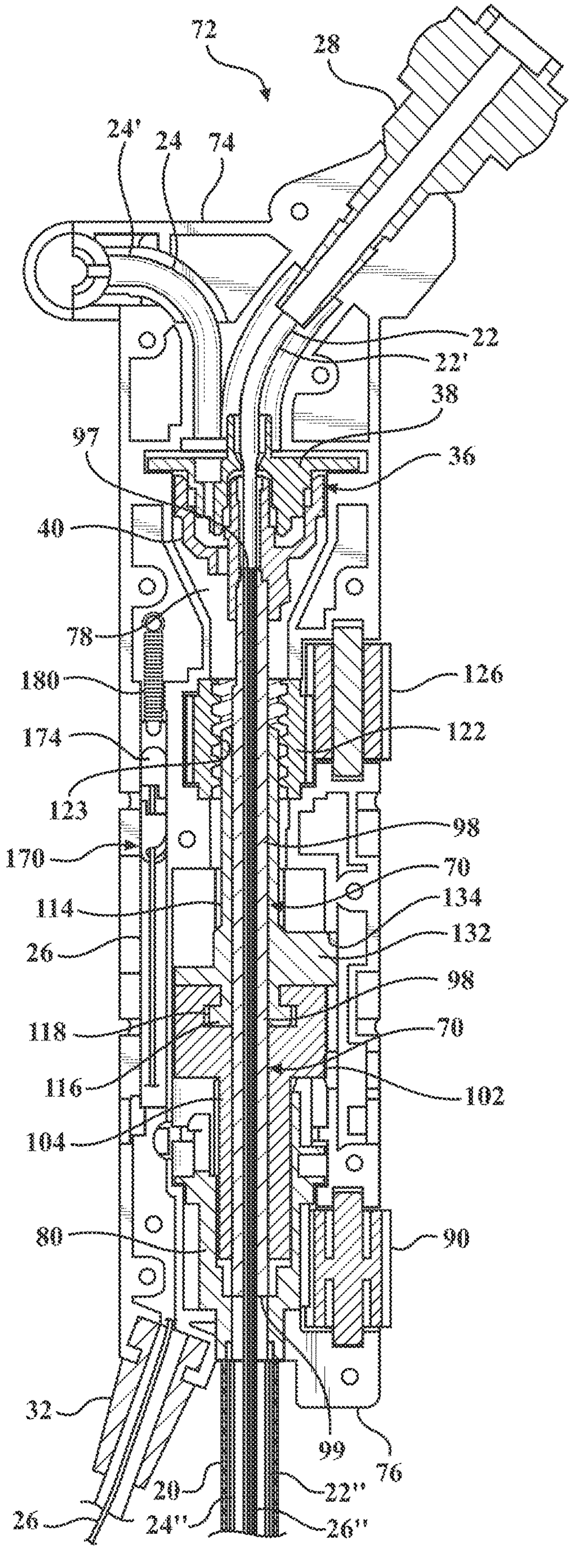
FIG. 23 is a cross-sectional view of the control case of FIG. 19 additionally illustrating the union reservoir cap and hub of the lumen interruption mechanism, the threaded gear, the lead screw, the anchor arm and the center gear in cross-section to more clearly illustrate the alternative embodiment of the synchronous rotation mechanism including an axle extending from a proximal axle end directly connected to the union reservoir hub and a distal axle end directly connected to the center gear for establishing simultaneous and synchronous rotation of these directly connected components.

For example, as best illustrated in FIGS. 19 and 23, the control assembly 10 can include a single, inner spur gear 90 for establishing the operable coupled relationship between the rotation control knob 86 and the center gear 80. However, as best illustrated in FIG. 2, the control assembly could include the inner spur gear 90 plus an additional, adjacent spur gear 92 which are sequentially disposed between the rotation control knob 86 and the center gear 80 to establish the operable interconnection therebetween. The use of the additional, adjacent spur gear 92 allows rotation of the rotation control knob 86 to distribute rotation of the center gear 80 in the same rotational direction.

More specifically, as illustrated in FIG. 2, each of the inner spur gear 90 and the adjacent spur gear 92 are disposed radially inward from the rotation control knob 86 such that their respective axis of rotation are aligned with one another, as well as the central axis A, in parallel (but radially spaced) relationship. As a result, the rotation knob gear teeth 88 are disposed in operable connection with the inner spur gear 90, which is disposed in operable connection with the adjacent spur gear 92, which is in operable connection with the center gear 80 to drive rotation of the catheter shaft 20 about the axis A in the same direction as the rotational direction of the rotation control knob 86. The diameters of this power train are designed to a desired output ratio.

The synchronous rotation mechanism 70 is disposed in operably coupled relationship with the union reservoir hub 40 of the lumen interruption mechanism 36 and the center gear 80 to simultaneously and synchronously drive rotation of the union reservoir hub 40 in response to rotation of the center gear 80 (and the catheter shaft 20 coupled thereto) via the rotation control knob 86. As best illustrated in FIGS. 2, 19 and 23, the synchronous rotation mechanism 70 includes an axle 98 extending from a proximal axle end 97 operably coupled with the union reservoir hub 40 to a distal axle end 99 operably coupled with the center gear 80. The axle 98 is rotatable in response to rotation of the center gear 80 to establish the synchronous rotation of the union reservoir hub 40.

Figure 25:
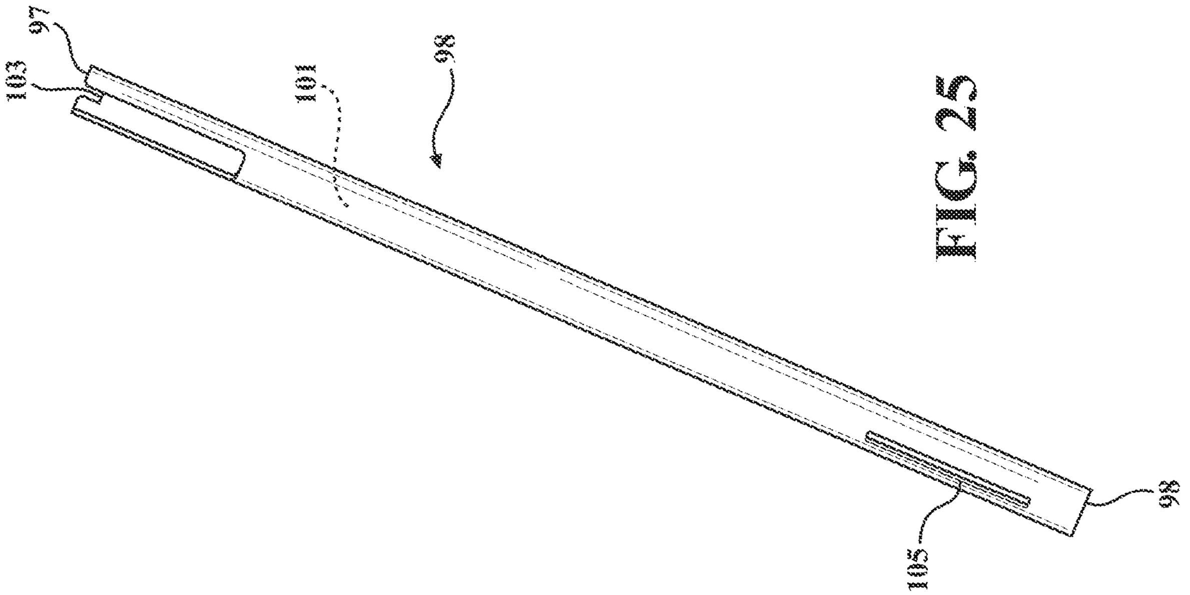
FIG. 25 is a perspective view of the axle in the alternative embodiment of the synchronous rotation mechanism.
Figure 24:
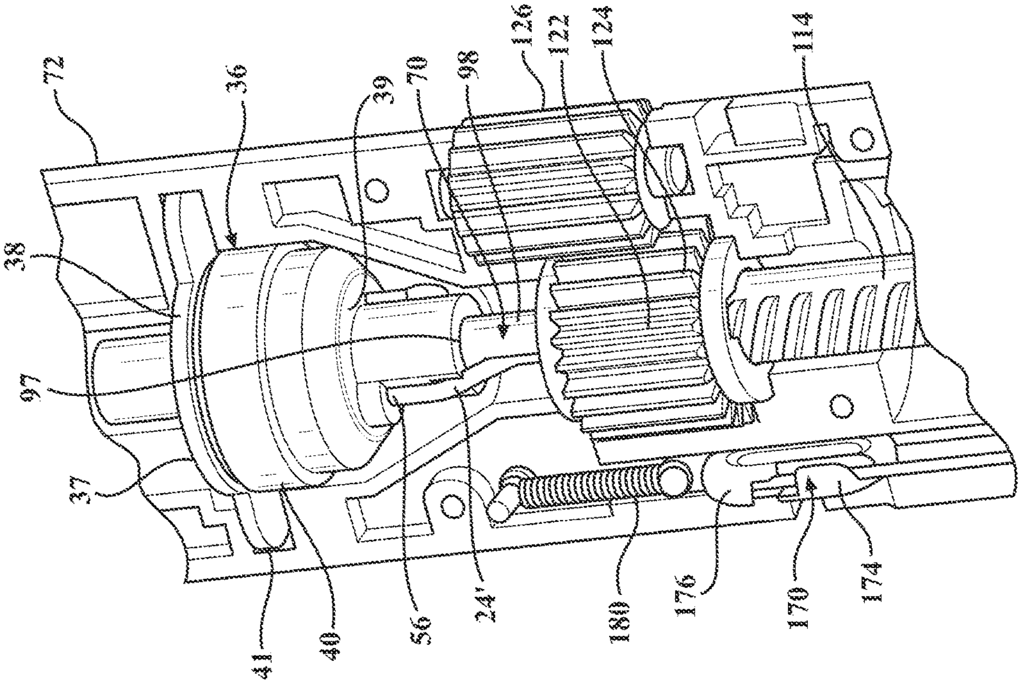
FIG. 24 is a magnified perspective cross-sectional view of a portion of FIG. 19.

More specifically, as best illustrated in FIGS. 19, 23 and 25, in accordance with a first embodiment of the synchronous rotation mechanism 70, the axle 98 extends within the control compartment 78 in aligned relationship with the axis A such that the proximal axle end 97 is directly connected to the union reservoir hub 40 and the distal axle end 99 is directly connected to the center gear 80. In this arrangement, rotation of the center gear 80 by the rotation control knob 86 results in a direct drive of the union reservoir hub 40 via the axle 98. The direct drive axle 98 is preferably comprised of a rigid tubular structure strong enough to distribute torque from the center gear 80 to which it is attached distally to the union reservoir hub 40 to which it is attached proximally. As will be appreciated in view of the second embodiment of the synchronous rotation mechanism 70, use of the direct drive axle 98 simplifies a structure of the synchronous rotation mechanism 70 through use of a single component as opposed to requiring multiple components to establish synchronous rotation of the union reservoir hub 40 with the center gear 80. As further illustrated in FIGS. 19-20 and 23, the arrangement of the tubular-shaped axle 98 along the axis A also allows the working channel 22, the fluid channel 24, and/or the electronics cable 26 to pass through the axle 98. More specifically, the axle 98 defines an internal component passageway 101 extending between the proximal and distal axle end 97, 99, such that the dynamic portions 22", 24" of the working and fluid channel components 22, 24 can extend from their respective hub outlets 48, 54, pass through the internal component passageway 101 and into the catheter shaft 20 (which is coupled to the center gear 80). As will be described in more detail below, in an arrangement, the dynamic portion 26' of the electronics cable 26 could also pass from the lumen interruption mechanism 36 and into the internal component passageway 101 for routing to the catheter shaft 20. As further illustrated in FIG. 25, the proximal axle end 97 of the axle 98 in the first embodiment of the synchronous rotation mechanism 70 can include a castellation feature 103 for establishing a mechanical interface and torque distribution to the union reservoir hub 40 via the direct connection. The distal axle end 99 of the axle can also include a breakout slot 105 for allowing any of the working components to break out of the interior component passageway 101 as needed to make their connections to the complementary components of the control assembly 10.

As best illustrated in FIG. 2, in accordance with a second embodiment of the synchronous rotation mechanism 70, the proximal and distal axle ends 97, 99 of the axle 99 are indirectly connected to the union reservoir hub 38 and center gear 80, respectively. More specifically, in this second embodiment of the synchronous rotation mechanism 70, the union reservoir hub 40 defines a set of hub gear teeth 94 extending radially outwardly from the union reservoir hub 40 in circumferentially aligned relationship about the central axis A. The synchronous rotation mechanism 70 includes a proximal spur gear 96 disposed on the proximal axle end 97 of the axle 98, radially outward from the union reservoir hub 40 and in operable engagement with the hub gear teeth 94. The distal axle end 99 of the axle 98 is connected to the adjacent spur gear 92 that is operably interconnected with the center gear 80, which is used to drive rotation of the center gear 80 via rotation of the rotation control knob 86 in accordance with an arrangement, as previously described. The proximal spur gear 96 is rotatable by the axle 98 about an axis of rotation that is parallel and radially spaced with the central axis A, and axially aligned with the axis of rotation of the adjacent spur gear 92. Put another way, the proximal spur gear 96 and the adjacent spur gear 92 are disposed in axially aligned relationship for rotation about a shared axis of rotation. The axle 98 extends axially between the adjacent spur gear 92 and the proximal spur gear 96 along this shared axis of rotation to synchronously and simultaneously drive rotation of the proximal spur gear 96 via rotation of the adjacent spur gear 92 driven by the rotation control knob 86. The proximal spur gear 96 is configured to have the same design and radial orientation as the adjacent spur gear 92 to result in simultaneous equivalent rotation. The hub gear teeth 94 of the union reservoir hub 40 are also identical in size, number and diameter to the center gear teeth of the center gear 80. In this way, rotation of the center gear 80 results in 1:1 rotation of the union reservoir hub 40 and therefore the catheter shaft 20 connected to the center gear 80 and the working components coupled to the union reservoir hub 40 move in synchronicity in response to rotation of the rotation control knob 86 by a user of the control assembly 10.

Similar to the winding and overlapping problem discussed immediately above with respect to the dynamic portions of the working and fluid channels 22", 24", torsion and kinking of the at least one electronics cable 26 during rotation of the catheter shaft 20 can also lead to failure and compromised performance of this working component. Accordingly, the control assembly 10 also includes a cable take-up assembly 60 configured to enable rotation of the catheter shaft 20 without adversely winding the electronics cable 26 and without the additional requirement of a joint and connectors along the electronics cable 26 to achieve this objective, namely because different from the working and fluid channels 22, 24, it is often not practical to interrupt or bifurcate the wires within the electronics cable 26. As best illustrated in FIGS. 2 and 19, the cable take-up assembly 60 is disposed in the control compartment 78 of the control case 72 and is rotatable about the axis A synchronously with the union reservoir hub 38 and the center gear 80. The cable take-up assembly 60 defines a spool 62 extending circumferentially about the axis A, and the electronics cable 26 is routed to and around the spool 62 between the static portion 26' and the dynamic portion 26". As illustrated in FIGS. 11A-B and FIGS. 22B-C, and described in more detail below, synchronous rotation of the cable take-up assembly 60 with the union reservoir hub 38 and the center gear 80 in a first rotational direction winds the electronics cable 26 around the spool 62 and synchronous rotation of the cable take-up assembly 60 in a second opposite rotational direction unwinds the electronics cable 26 from the spool 62 for allowing the dynamic portion 26" of the electronics cable 26 which passes from the cable take-up assembly 60 to the distal tip 21 of the catheter shaft 20 to maintain a position relative to the dynamic portions of the working and fluid channel components 22", 24" during their collective, simultaneous rotation with the catheter shaft 20. As illustrated in FIGS. 2-4 and 9-11B, in accordance with a first embodiment, the cable take-up assembly 60 can be implemented as an integrated component of the lumen interruption mechanism 36, and thus a combined functionality component. However, as best illustrated in FIGS. 19-20 and 22A-C, in accordance with a second embodiment, the cable take-up assembly 60 could also be a separate component located elsewhere within the control assembly 10 from the lumen interruption mechanism 36, in this case on the center gear 80. This is because in practice the functionality of the cable-take-up assembly 60 is independent of the lumen interruption mechanism 36 (other than the rotational synchronicity) and can exist as a separate component(s) in similar applications.

Figure 10:
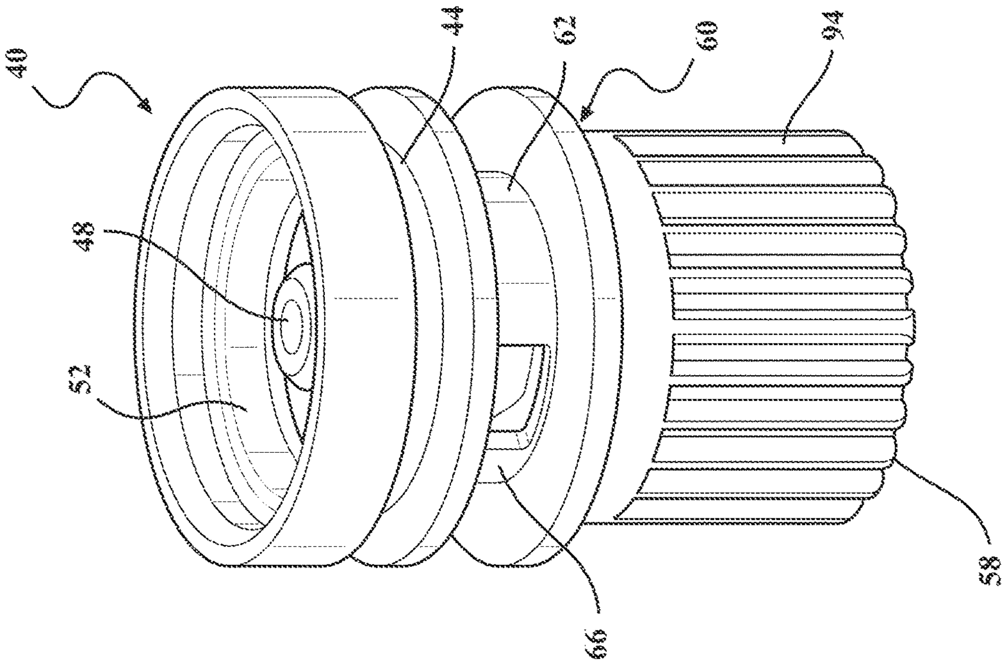
FIG. 10 is a perspective view of the union reservoir hub and the cable-take-up assembly.
Figure 9:
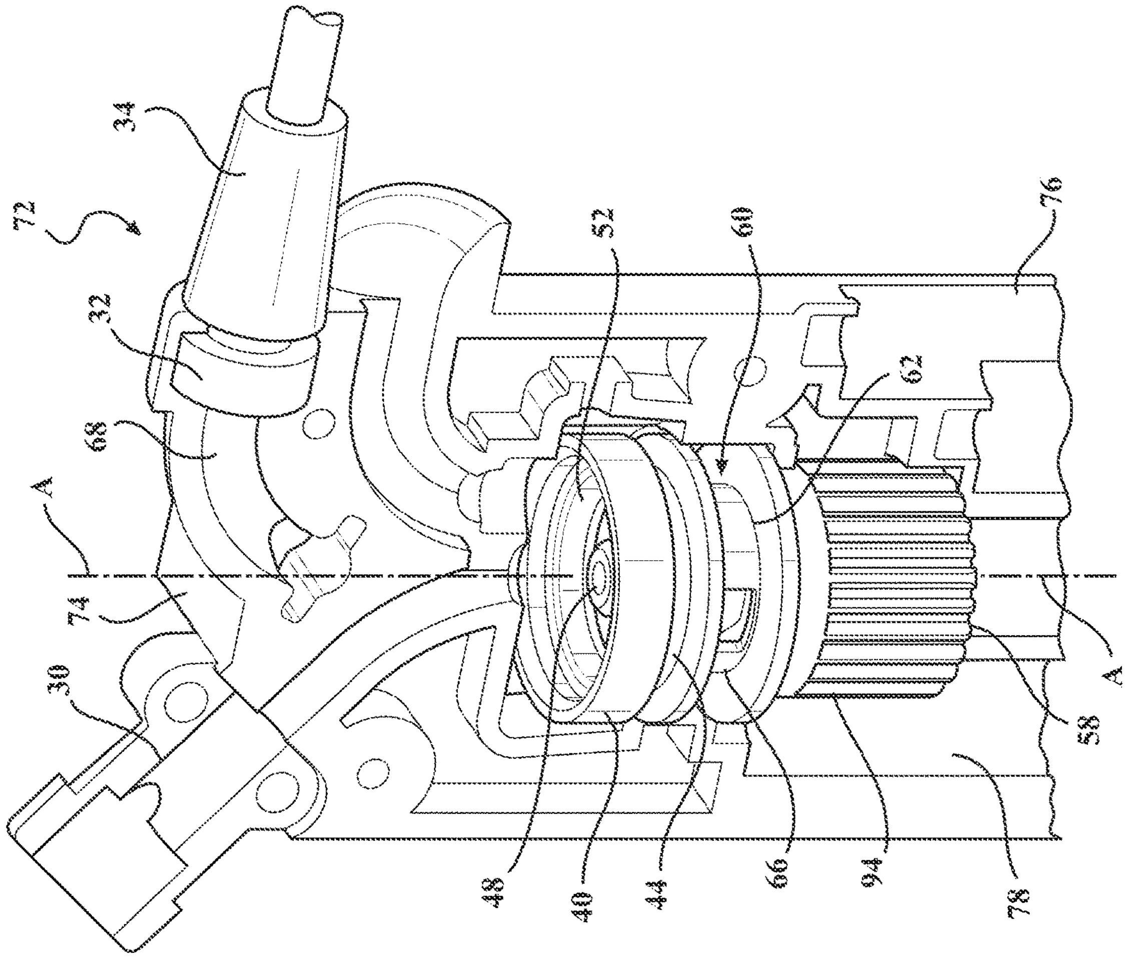
FIG. 9 is a partial cross-sectional perspective view of the control case illustrating the union reservoir hub disposed adjacent the proximal case end and with the union reservoir cap removed to more clearly illustrate the circumferentially shaped fluid reservoir.
Figure 11B:
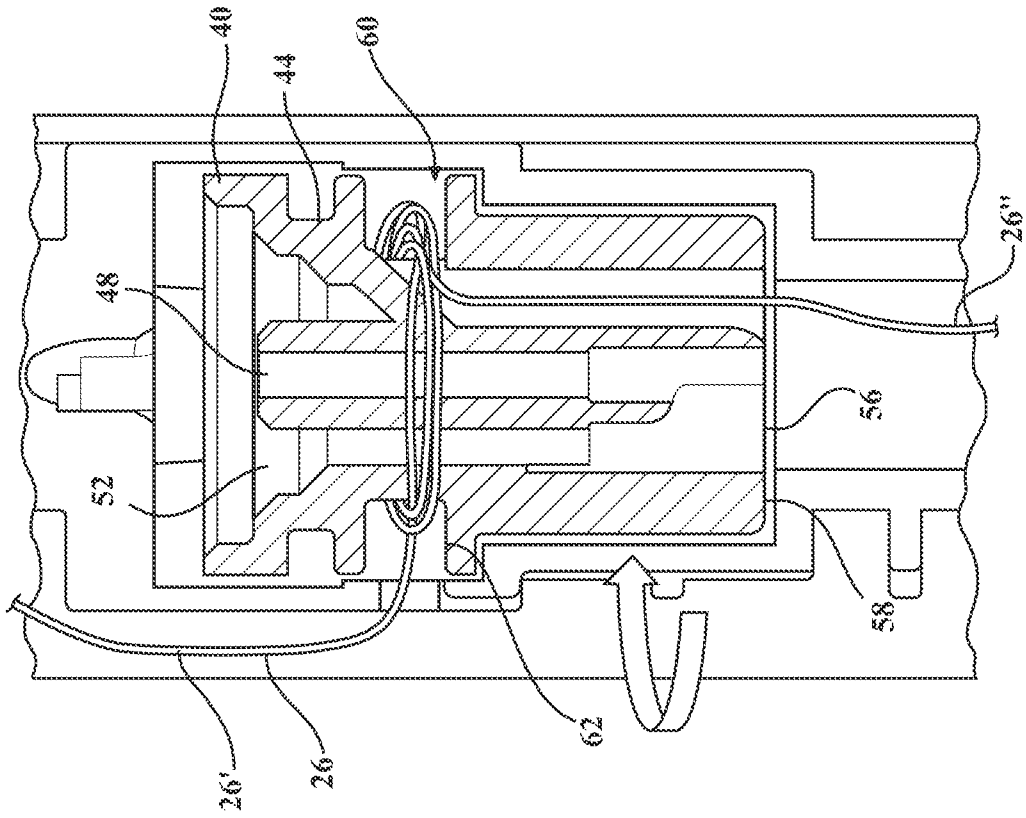
FIG. 11B is a cross-sectional view of the lumen interruption mechanism illustrating operation of the cable take-up assembly during rotation about the axis in a second rotational direction opposite the first rotational direction.
Figure 11A:
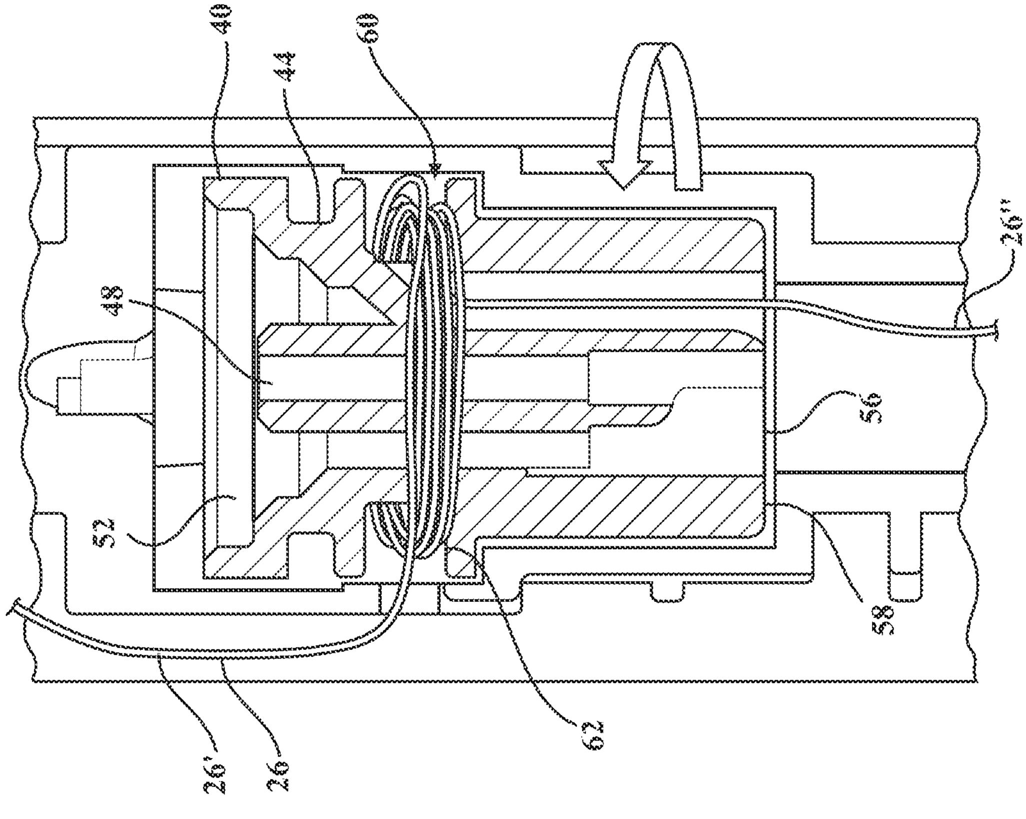
FIG. 11A is a cross-sectional view of the lumen interruption mechanism illustrating operation of the cable take-up assembly during rotation about the axis in a first rotational direction.

As best illustrated in FIGS. 9-11, in the first embodiment of the cable take-up assembly 60, the spool 62 is defined by the union reservoir hub 40 and extends radially inwardly from an exterior surface of the union reservoir hub 40 and circumferentially about the axis A. A spool slack chamber 64 is defined between an interior surface of the spool 62 (as defined by an inner diameter of the union reservoir hub 40) and an interior surface of the control assembly 10, disposed adjacent the cable take-up assembly 60. As will be understood in view of the following discussion of operation, the interior surface of the control assembly 10 used to define an exterior wall of the slack chamber 64 provides a barrier to limit the build-up of excessive slack in the slack chamber 64 during rotation of the spool 62. The spool 62 defines a window 64 disposed in both communication with this slack chamber 66 as well as an electronics cable passage 37 that extends from the lumen interruption mechanism 36 to the electronics port 32. The electronics cable 26 is routed such that a distal length extends from the distal tip 21 of the catheter shaft 20 to the union reservoir hub 40 of the lumen interruption mechanism 36, with a medial length of the electronics cable 26 then wound loosely around the spool 62 a predetermined number of times such that the wound electronics cable 26 is housed within the spool slack chamber 66. A proximal length of the electronics cable 26 then continues from the slack chamber 66, through the window 64 and extends through the electronics cable passage 37 to be routed through the strain relief 34 and ultimately be affixed to a static PCB. As will be explained above, use of the cable take-up assembly 60 provides for the distal length of the electronics cable 26 to rotate in unison with the catheter shaft 20 such that the electronics cable 26 never winds around other working components, such as the dynamic working and fluid channels 22, 24. In addition, the cable take-up assembly 60 advantageously allows for the use of one, continuous electronics cable 26 extending through the control assembly 10, without the need for electrical connectors.

As best illustrated in FIG. 11, in operation, rotation of the cable take-up assembly 60 in one direction (in this case synchronously with rotation of the union reservoir hub 40) takes up the slack in the spool 62 to facilitate safe rotation of the catheter shaft 20, while rotation of the cable take-up assembly 60 in the other direction (again synchronously with corresponding rotation of the union reservoir hub 40) unwinds and loosens the loops of the electronics cable 26 around the spool 62. As the cable take-up assembly 60 rotates, the window 66 acts to guide the electronics cable 26 around the spool 62. Put another way, the window 66 acts like an eyelet, forcing the electronics cable 26 to rotate in association with the union reservoir hub 40. The number of cable winds corresponds to the amount of limitation required by the control assembly 10, which can be greater than 360 degrees if necessary, but not practically infinite. As a result, the cable take-up assembly 60 minimizes the torque and winding condition on the electronics cable 26 breaking out from the catheter shaft 20 and which otherwise would occur during rotation of the catheter shaft 20.

As mentioned previously, in accordance with a second embodiment, the cable take-up assembly 60 is implemented on the center gear 80 as opposed to on the lumen interruption mechanism 36. (See FIGS. 19-20 and 22A-C). In regards to the electronics cable, there are many types of electronics cables that might be used in the control assembly 10. Some electronics cables are more resistant to bending, some are more prone to kink, some are more supple and less inclined to react predictably to "push forces", etc. In instances where the mechanical characteristics of the electronics cable do not lend themselves as favorable to the unwinding action described above, particular failure modes might occur. This can manifest in the clockwise (first rotational direction) and counterclockwise (second rotational direction) of the cable take-up assembly 60, with the back and forth of the electronics cable in tension followed by compression (push) resulting in knotting and accumulation of the electronics cable within the spool 62. The end effect can be a loss of degradation of image signal due to the knotting, to worst case scenario of the knotting decreasing the total free length of the cable and resulting in fracture of the electronics cable and full loss of function of the electronics.

As best illustrated in FIGS. 19-23, the control assembly 10 implements a solution to this problem, namely routing the static portion 26' of the electronics cable 26 through a cable tensioning mechanism 170 prior to the spool 62 to continually apply a small amount of tension to the electronics cable 26 regardless of the rotational direction of the spool 62 and always maintain the electronics cable 26 taught against an inner diameter of the spool 62, in all instances. In other words, the cable tensioning mechanism 170 keeps the electronic cable 26 in tension with the spool 62, and prevents the "push" phase of rotation of the spool 62 from bringing in the variability that might result in knotting.

Figure 21:
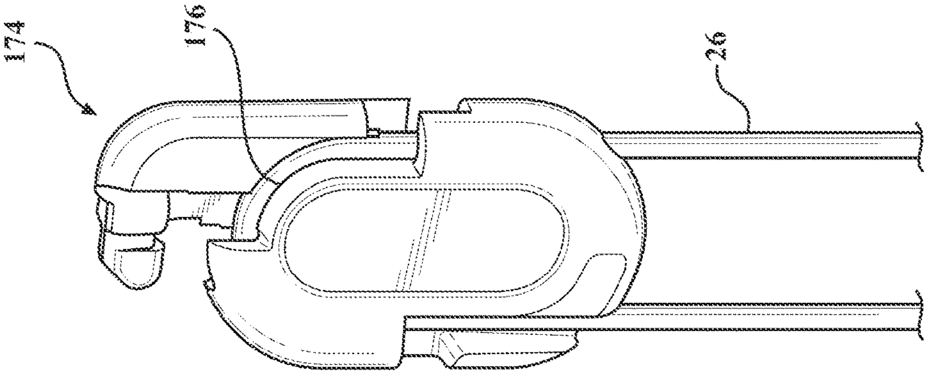
FIG. 21 is a perspective view of a loop of the alternative embodiment of the cable take-up assembly.
Figure 20:
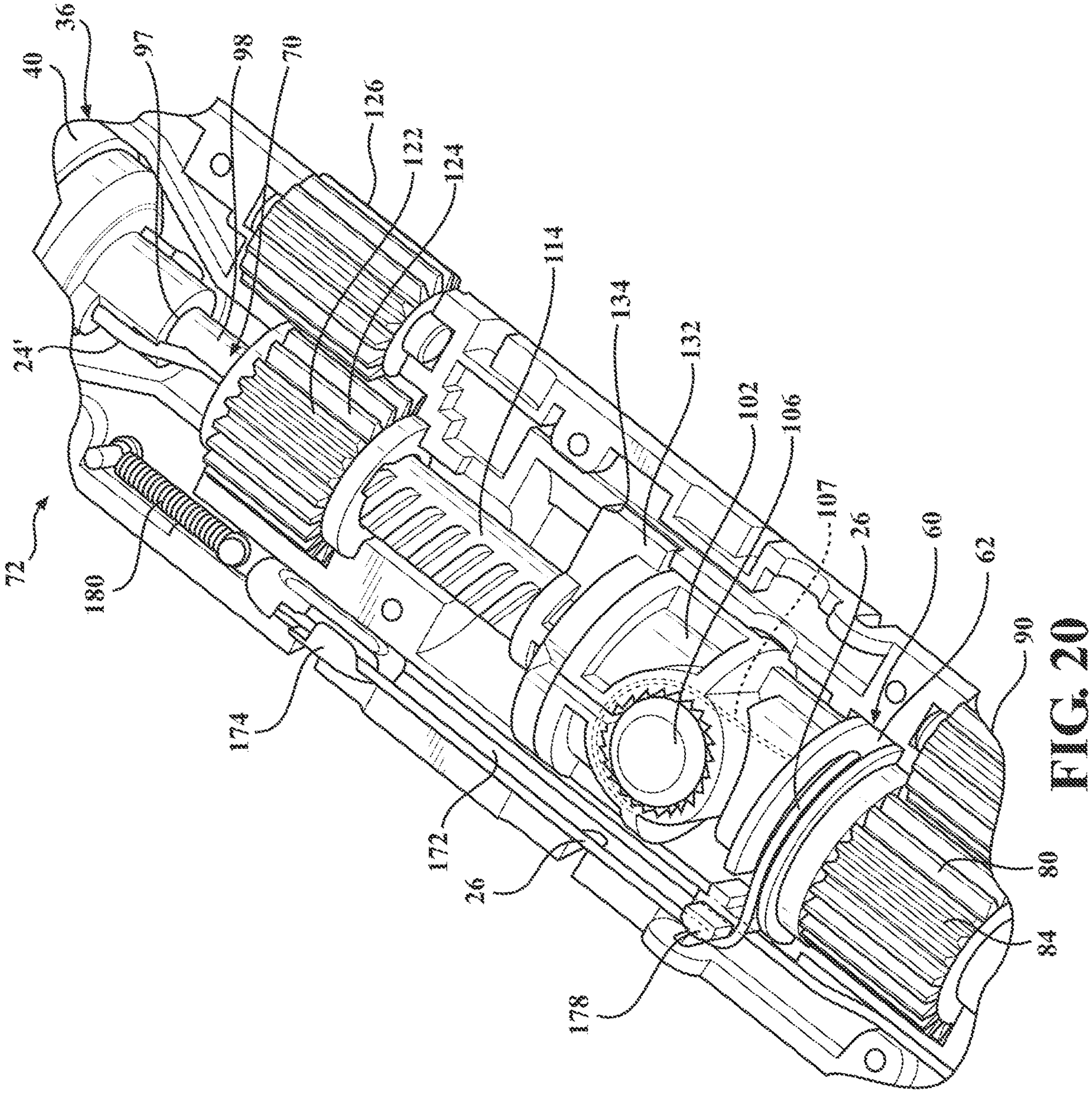
FIG. 20 is a magnified perspective view of a portion of FIG. 19 more clearly illustrating the alternative embodiment of the cable take-up assembly.

More specifically, as best illustrated in FIGS. 19-20, the control case 72 defines a tensioning channel 172 extending in generally parallel and radially spaced relationship with the axis A between the proximal and distal case ends 74, 76. When the static portion 26' of the electronics cable 26 enters the control case 72 via the distal case end 76, the tensioning channel 172 is disposed in communication with the electronics port 32 and extends from the distal case end 76 towards the proximal case end 74. However, the directional arrangement of the tensioning channel 172 could be reversed, and extend from the proximal case end 74, if the electronics cable 26 entered the control case 72 via an electronics port 32 disposed at the proximal case end 74 (such as shown in FIG. 2). The cable tensioning mechanism 170 is disposed in the tensioning channel 172 and includes a loop component 174 biased away from the electronics port 32 (in this case towards the proximal case end 74) and in a direction away from where the static portion 26' of the electronics cable 26 enters the control case 72. As best illustrated in FIG. 21, the loop component 174 defines a radiused portion 176, such that the static portion 26' of the electronics cable 26 is routed from the electronics port 32 through the tensioning channel 172 and to the loop component 174 at which point the electronics cable 26 passes over the radiused portion 176 to redirect the electronics cable from one direction to another and back along the tensioning channel 172 for routing to the spool 62. As best illustrated in FIG. 20, when the electronics cable 26 is routed back adjacent the spool 62, the electronics cable 26 passes around a shoulder 178 to assist in re-directing the electronics cable 26 transversely from the tensioning channel 172 and towards the spool 62

As illustrated in FIG. 21, the radiused portion 176 of the loop compartment 174 is preferably 180 degrees, to establish that most practical re-direction of force application.

However, this redirection of the electronics cable path could be any angle off the major axis to apply a tensile load, but is most effective for direction changes greater than 45 degrees and up to but not including an angle that would put the electronics cable back in line with its major axis, i.e., 360 degrees. The design of this loop component 174 is such that the electronics cable 26 can be installed without the need to pass both ends of the electronics cable 36 through the radiused portion 176, i.e., the electronics cable 26 can be affixed to the loop component 174 anywhere mid-section of the electronics cable 26.

As further illustrated in FIGS. 19-20, the tensioning mechanism 170 includes a biasing member 180, such as a spring, or the like, extending between the control case 72 and the loop component 174 to establish the biased relationship away from the electronics port 32, and apply a counter force to the loop component 174 in movement and therefore to the electronics cable 26 routed around the radiused portion 176. If the biasing member 180 is a tension spring, the tension spring is attached to the loop component 174 above the radiused portion 176 (such as shown in FIGS. 19-20). However, if the biasing member 180 is a compression spring, the compression spring would be attached below the radiused portion 176, without departing from the scope of the subject disclosure.

Figure 22C:
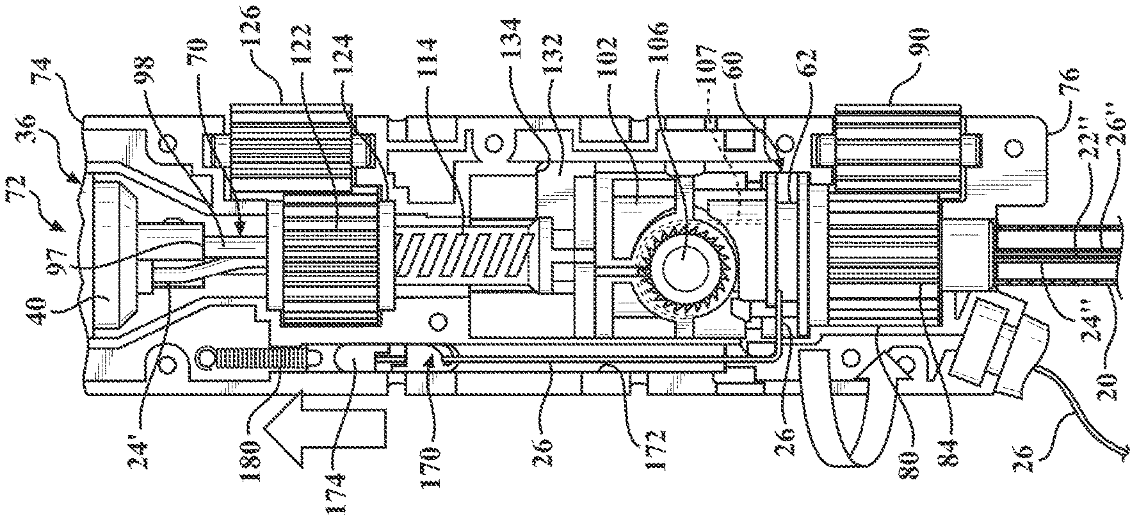
FIG. 22C is a cross-sectional view of the control case illustrating operation of the second embodiment of the cable take-up assembly during rotation about the axis in a second rotational direction opposite the first rotational direction.
Figure 22B:
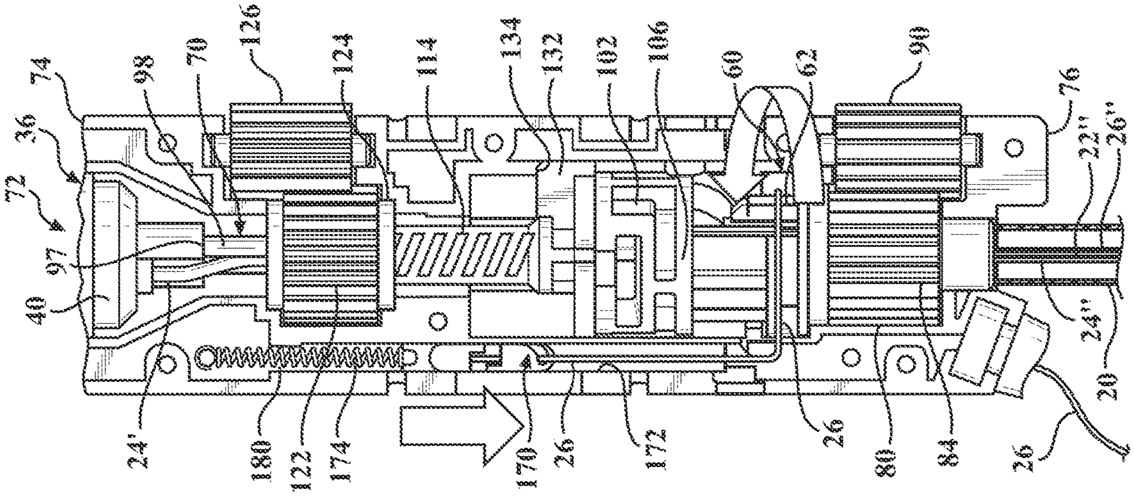
FIG. 22B is a cross sectional view of the control case illustrating operation of the second embodiment of the cable-take up assembly during rotation about the axis in a first rotational direction.
Figure 22A:
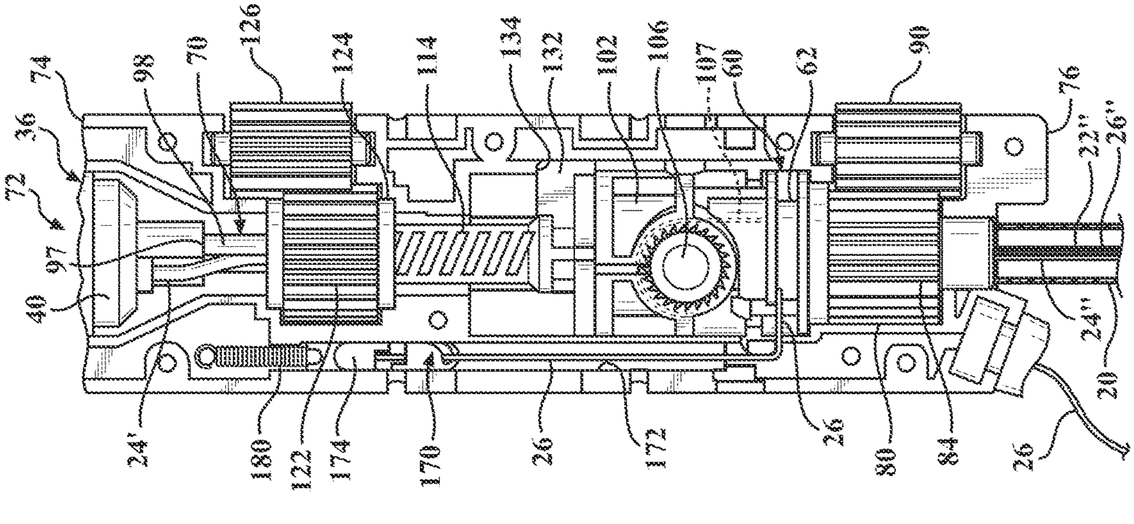
FIG. 22A is a cross-sectional view of the control case illustrating the second embodiment of the cable take-up assembly disposed in a static condition.

As illustrated in FIGS. 22A-22C, during operation, rotation of the cable take-up assembly 60 and the associated spool 62 in a first rotational direction (as shown in FIG. 22B) winds the electronics cable 26 around the spool 62, foreshortening a length between the spool 62 and the loop component 174 and causing the loop component 174 to be displaced along the tensioning channel 172 in a direction towards the spool 62. This displacement is resisted by the biasing member 180 and a tensile force is distributed to the electronics cable 26, such that the electronics cable 36 is never allowed to have enough slack to entangle or knot. As shown in FIG. 22C, changing direction of rotation of the cable take-up assembly 60 and the associated spool 62 in the opposite rotational direction un-wraps the electronic cable 26 from the spool 62 and results in the loop component 174 moving in the opposite linear direction (via the biasing force applied by the biasing member 180), reducing the tensile force applied to the electronics cable 26. As the spool 62 passes over center, the direction of the wrap around the spool 62 changes while the loop component 174 repeats its linear cycle applying the tensile load. In this way, as the cable take-up assembly 60 cycles through the full range of rotation, the loop component 174 cycles up and down, like a piston, continually applying a tensile load to the electronics cable 26 to always keep the electronics cable 36 taught against the spool 62 and prevent entanglement and knotting.

Figure 14:
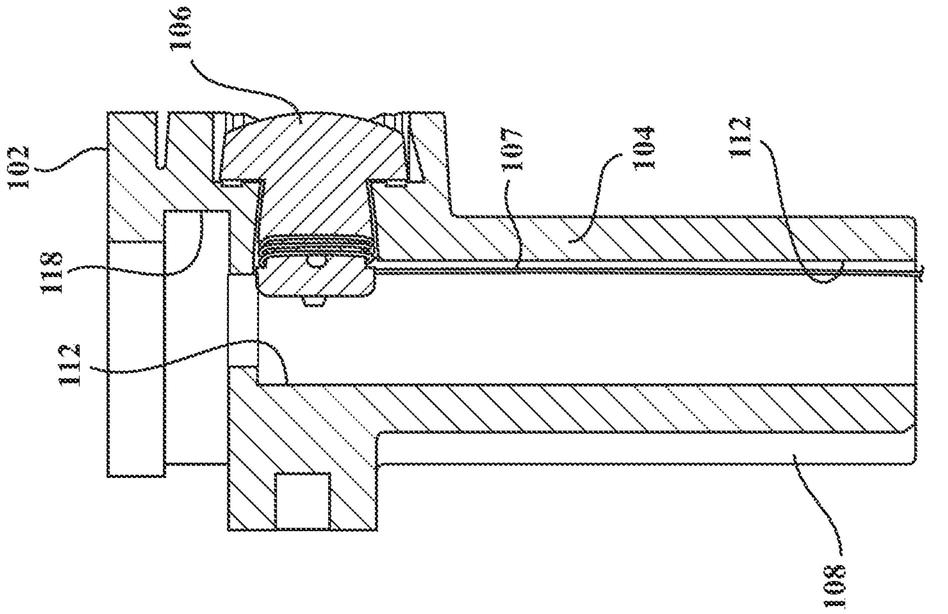
FIG. 14 is a cross-sectional view of the anchor arm and the anchor shaft.
Figure 13:
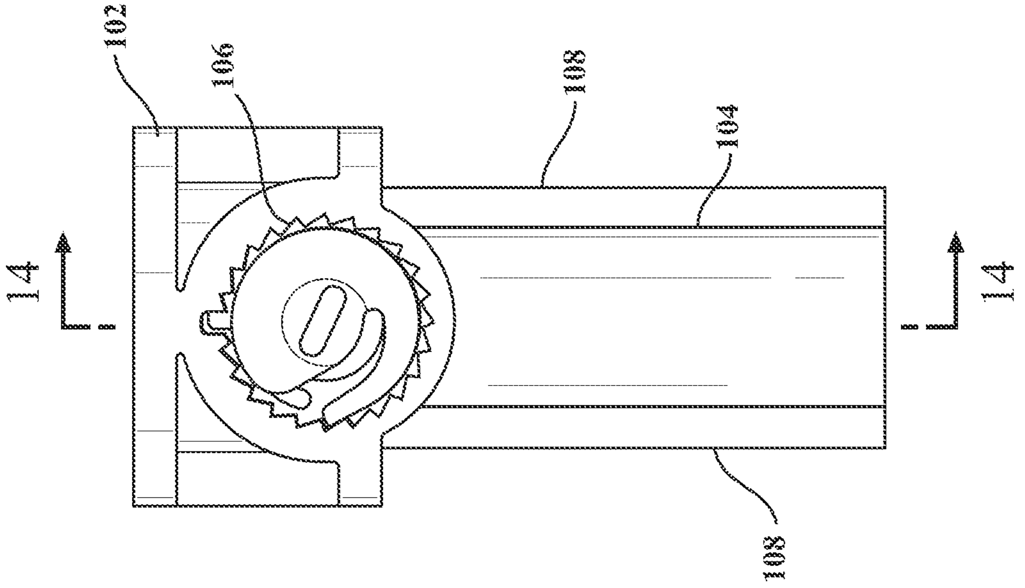
FIG. 13 is a side view of an anchor arm and an anchor shaft.
Figure 26B:
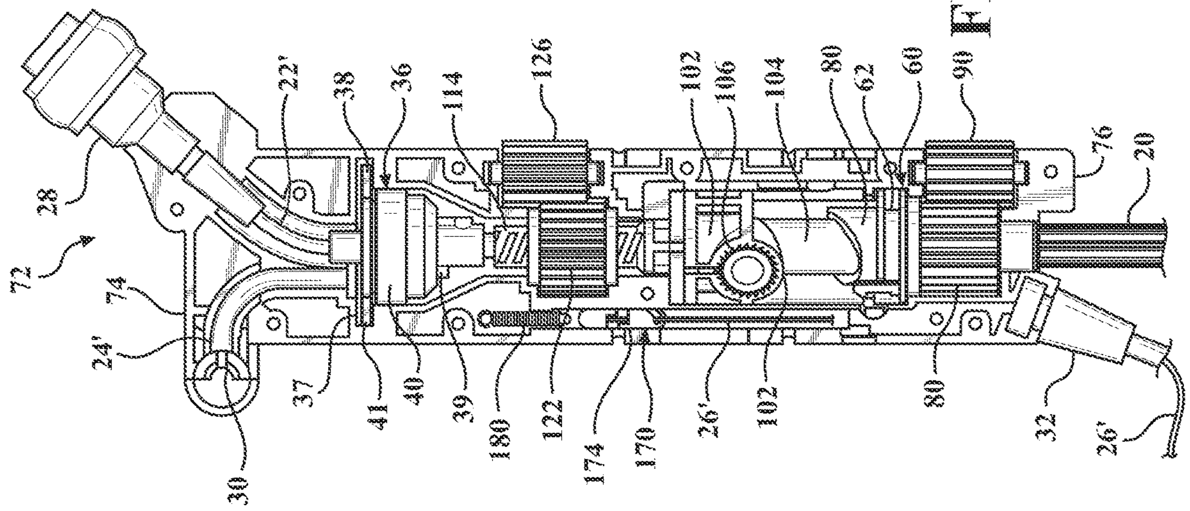
FIG. 26B is a perspective cross-sectional view of the control case illustrating a lead screw and an anchor arm axially displaced in the proximal direction relative to the center gear in response to rotation of a threaded gear operably coupled to a deflection control knob to apply a resultant tension to a pull wire secured to the anchor arm for deflecting the distal tip of the catheter shaft.

As illustrated in FIGS. 1 and 1A, the handle 85 of the control assembly 10 also includes a deflection control knob 100 rotatably disposed about the proximal case end 74 of the control case 72 to effectuate deflection of the distal tip 21 of the catheter shaft 20 in response to rotation of the deflection control knob 100 by the user. As best illustrated in FIGS. 2, 19 and 26B, the control case 72 includes an anchor arm 102 disposed within the control compartment 78 adjacent a proximal end of the center gear 80 and having an anchor shaft 104 extending axially downwardly into the center gear passageway 82. At least one pull wire 107 extends from the anchor arm 102 into the catheter shaft 20 and ultimately terminates at the distal tip 21. As best illustrated in FIGS. 13, 14 and 19, a pull wire tensioning mechanism 106 is provided for fixing the pull wire 107 to the anchor arm 102, and allowing an operator to modify a length of the pull wire 107 between the anchor arm 102 and the distal tip 21 in order to provide a base tension of the pull wire 107 that correlates with a desired adjustment sensitivity of the pull wire. A preferred arrangement of the pull wire tensioning mechanism 106 is described in U.S. application Ser. No. 17/150,346, such as in Paragraph [0067], the disclosure of which is incorporated herein by reference.

As best illustrated in FIGS. 2, 13 and 14, the anchor shaft 104 defines at least one axial rib 108 extending radially outwardly from the anchor shaft 102 in aligned and radially spaced relationship with the central axis A. The center gear 80 defines at least one axial slot 110 extending radially inwardly from the center gear passageway 82 for receiving the at least one axial rib 108. Mating of the axial rib 108 with the axial slot 110 drives synchronous and simultaneous rotation of the anchor arm and shaft 102, 104 with the center gear 80, and also allows the anchor arm and shaft 102, 104 to translate proximally and distally relative to center gear 80 (as will be described in more detail below, and best illustrated in FIGS. 26A-B) while still maintaining rotational alignment between these components. As a result, the mating of the axial rib 108 with the axial slot 110 allows the anchor arm 102 to work in concert with the center gear 80 as well as the synchronous rotation mechanism 70 in such a way that the pull wire 107 maintains radial orientation with the catheter shaft 20, and is not buckled, kinked, or overlapped with the other working components during rotation of the catheter shaft 20 by the user via rotation of the rotation control knob 86.

Figure 12:
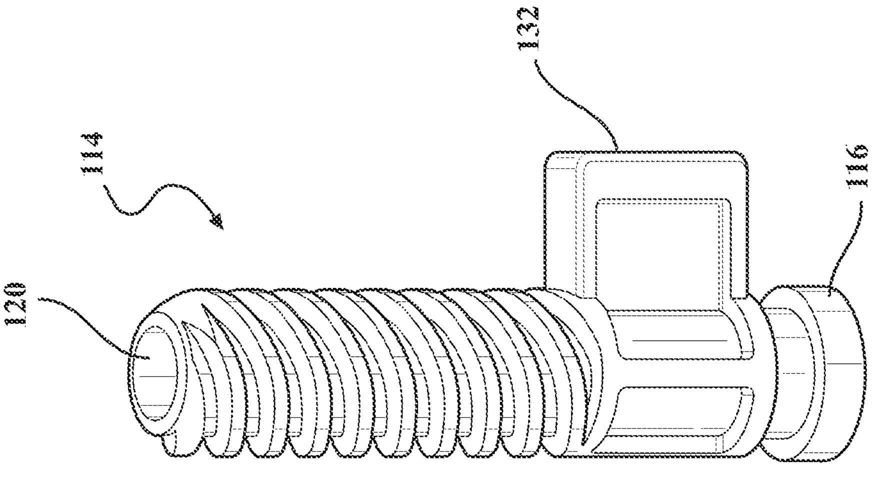
FIG. 12 is a perspective view of a lead screw.

As illustrated in FIGS. 13-14, the anchor arm 102 and anchor shaft 104 collectively define an anchor passageway 112 disposed in communication with the center gear passageway 82 for allowing the dynamic portions of the working components of the catheter to be received from the center gear passageway 82 and pass through the anchor passageway 112 into the control compartment 78. The control case 72 includes a lead screw 114 disposed within the control compartment 78 adjacent to a proximal end of the anchor arm 102 and having a rotor flange 116 disposed in coupled relationship with a circumferential slot 118 defined by an interior portion of the anchor arm 102 and which extends radially inward from the anchor passageway 112. (See FIG. 14). As will be appreciated in view of the following description, this joint holds the lead screw 114 and the anchor arm 102 together axially while also allowing full rotation of the anchor arm relative to the lead screw 114 (which is always maintained in a rotationally static position). As best illustrated in FIG. 12, similar to the center gear 80 and the anchor arm 102, the lead screw 114 also defines a lead screw passageway 120 that allows the dynamic portions of the working components of the catheter to pass along from the anchor passageway 112 towards the union reservoir hub 40 disposed proximally above.

As best illustrated in FIGS. 1A, 2, 19 and 26A-B, the control case 72 includes a threaded gear 122 disposed in rotationally aligned relationship about the central axis A and including an internal thread 123 disposed in threaded relationship with a proximal end of the lead screw 114. A set of threaded gear teeth 124 extend radially outwardly from the threaded gear 122, and at least one deflection spur gear 126, 128 is disposed in the control compartment 78 to establish the operably coupled relationship between the deflection control knob 100 and the threaded gear 122. For example, as illustrated in FIG. 19, in accordance with a first arrangement, only a first deflection spur gear 126 is arranged in radially offset relationship from and in operable relationship with both the threaded gear teeth 124 of the threaded gear 122 and the deflection control knob 100 to establish the operable coupling therewith. However, as best illustrated in FIGS. 1A and 2, in accordance with a second arrangement, an additional second deflection spur gear 128 can be sequentially arranged in radially offset relationship to the threaded gear 122. Put another way, as best illustrated in FIG. 2, the first deflection spur gear 126 is disposed radially offset from and in operable relationship with the threated gear teeth 124 of the threaded gear 122, and the second deflection spur gear 128 is disposed radially offset from an in operable relationship with the first deflection spur gear 126, such that rotation of the second (most radially offset) deflection spur gear 128 ultimately drives rotation of threaded gear 122. As previously mentioned, the handle 85 of the control assembly 10 also includes a deflection control knob 100 rotatably disposed about the proximal case end 74 of the control case 72. As best illustrated in FIG. 1A, this deflection control knob 100 includes a set of deflection knob gear teeth 130 circumferentially arranged along an inner diameter of the deflection control knob 100 and which are operably coupled with the first deflection spur gear 126 (in the first arrangement) or the second deflection spur gear 128 (in the second arrangement).

Figure 26A:
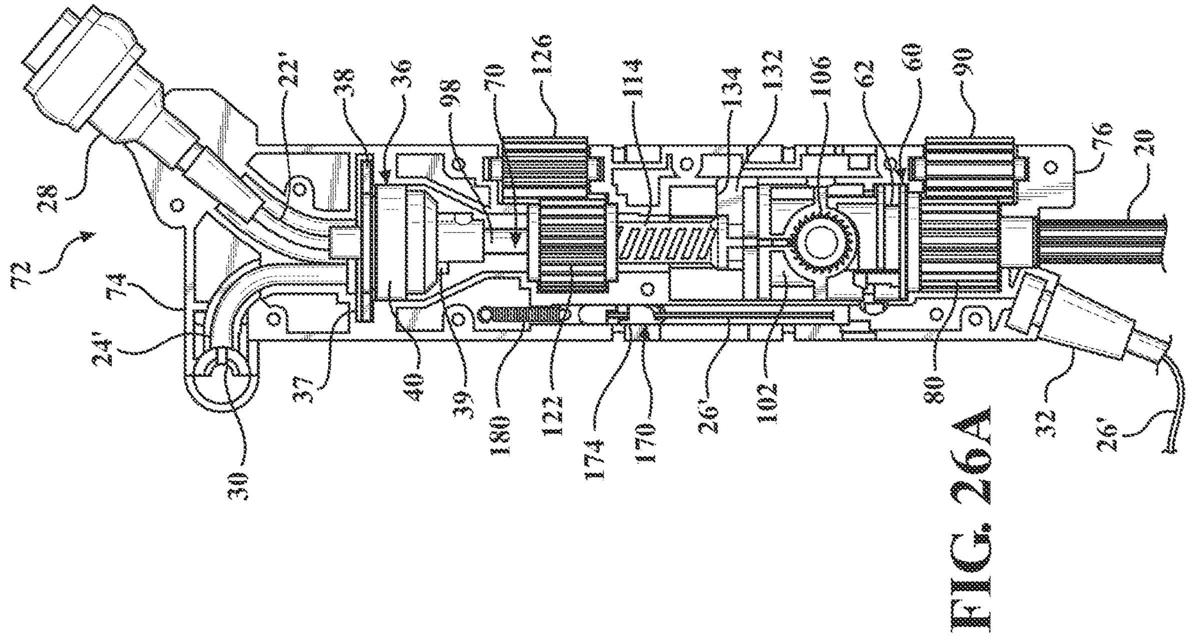
FIG. 26A is a perspective cross-sectional view of the control case.

As best illustrated sequentially in FIGS. 26A-B, in operation, rotation of the deflection control knob 100 ultimately drives rotation of the threaded gear 122, which is disposed in engaging relationship with the thread of the lead screw 114, resulting in axial displacement of the lead screw 114 both proximally and distally (depending on the rotational direction of the deflection control knob 100). When the lead screw 114 is axially displaced in the proximal direction (as shown in FIG. 26B), the anchor arm 102 is also axially displaced over the same distance by way of the coupling between the rotor flange 116 of the lead screw 114 and the circumferential slot 118 of the anchor arm 102, such that a resultant tension is applied to the pull wire 107 secured to the anchor arm 102 by way of this pulling motion. Thus, this axial displacement of the lead screw 114 over a distance effectuates the desired distal deflection curve in the distal tip 21 of the catheter shaft 20. For clarity, and as previously mentioned, the mating of the axial ribs and slot 108, 110 allows for axial movement of the anchor arm 102 relative to the center gear 80 and in conjunction with the lead screw 114 to effectuate the desired deflection.

As best illustrated in FIGS. 1A, 2, 12, 19 and 26A-B, the lead screw 114 includes an anti-torque wing 132 extending radially outwardly from the lead screw 114 and disposed in engaging relationship with a corresponding wing slot 134 disposed adjacent the lead screw 114 and defined by the control case 72 to prevent the lead screw 114 from rotating in response to movement by the threaded gear 122, and limit movement of the lead screw 114 to only the up (proximal) and down (distal) directions. As a result, torque is not distributed down to the pull wire to further prevent the pull wire from wrapping around other working components of the catheter. A pitch of the lead screw 114 and a pitch of the internal thread 113 of the threaded gear 122 is such that the friction angle remains intact, allowing the lead screw 114 to stay in place static when the deflection control knob 100 is not manipulated by a user.

Figures 15A, 15B, 15C:
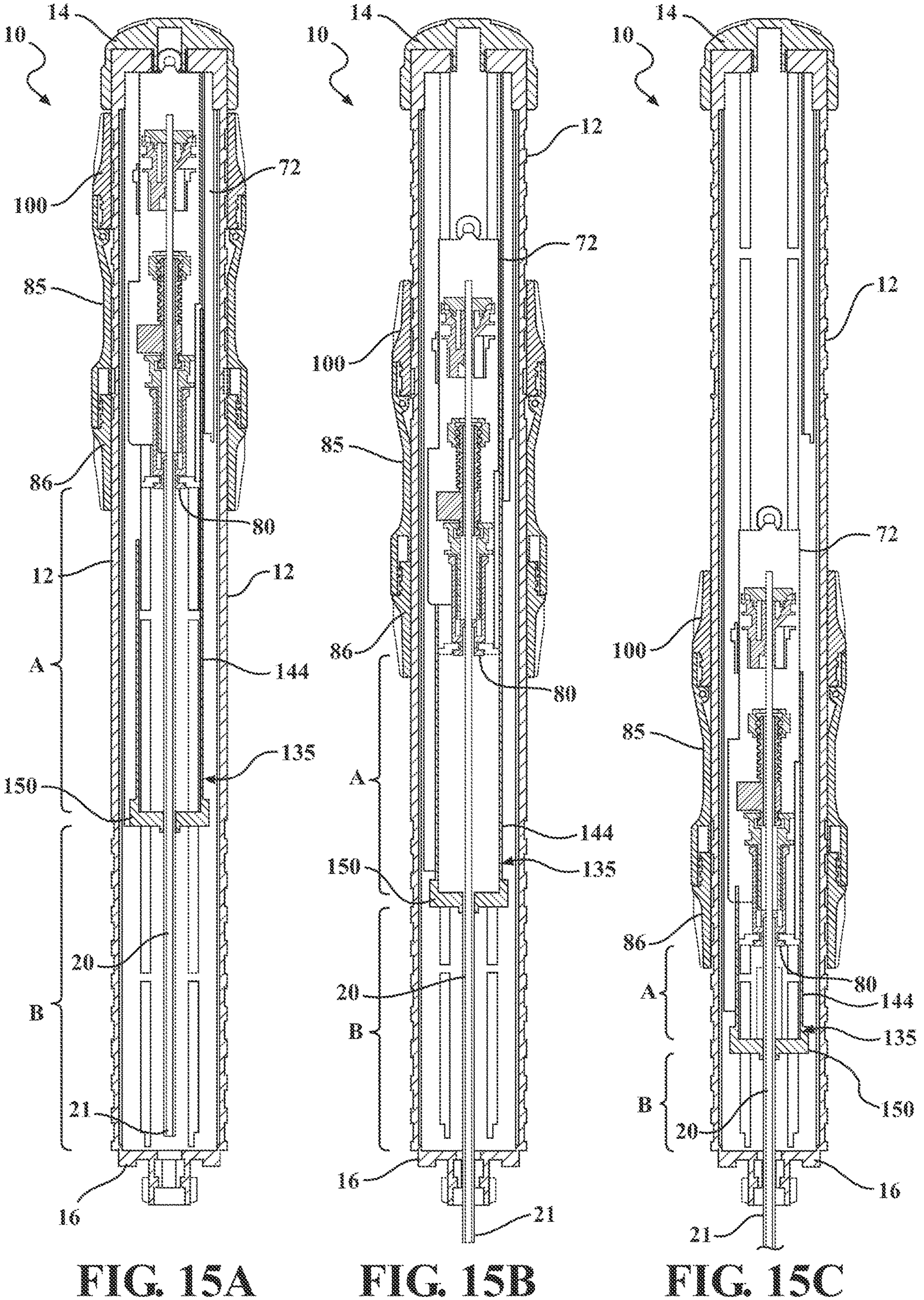
FIG. 15A illustrates a cross-sectional view of the control assembly.
FIG. 15B illustrates a cross-sectional view of the control case as the control case and the handle portion disposed in surrounding relationship with the control case translate axially towards the distal housing end to illustrate a proportional support mechanism consistently supporting the catheter shaft at a midpoint between the center gear and the distal end of the housing as the catheter shaft advances with the control case along the axis and the distal end of the catheter shaft exits the distal housing end.
FIG. 15C illustrates a cross-sectional view of the control case axially advanced to adjacent the distal housing end and the proportional support mechanism supporting the catheter shaft at a midpoint between the center gear and the distal end of the housing.

As best illustrated in FIGS. 15A-C, the control case 72 (which is surrounded by the handle 85) is axially translatable along the housing 12 from the proximal housing end 14 towards the distal housing end 14 to effectuate advancement and retraction of the catheter shaft 20, namely because the catheter shaft 20 is affixed to the center gear 80 and travels with the control case 72 during axial movement. As the control case 72 travels towards the distal housing end 14 of the housing 12, the distal tip 21 of the catheter shaft 20 is axially advanced by the user by way of translating the control case 72. However, during movement of the control case 72, a length of the catheter shaft 20 extending between the center gear 80 and the distal end 16 of the housing 12 is inclined to buckle, bend, and/or kink when a compressive load is applied to this length of catheter shaft 20, such as when the handle 85 is translated along the housing 12 by the user. The catheter shaft 20 has an amount of column strength by design to resist buckling and kinking, however the longer the distance between two points of support, the more side loading due to gravity, angular position of the catheter, user manipulation, etc. is inclined to move the catheter shaft 20 off its central axis A and decrease/defeat column strength.

The control assembly 10 includes a proportional support mechanism 135 disposed within the housing compartment 18 and continuously supporting the catheter shaft 20 at a point between the center gear 80 and the distal housing end 16 during the axial advancement of the catheter shaft 20 to provide additional point(s) of support consistently maintained along the length of catheter shaft 20 extending between the center gear 80 and the distal end 16 of the housing 12 across the entire range of travel of the control case 72 relative to the housing 12. Put another way, as the control case 72 moves towards the distal end 16 of the housing 12 to axially advance the distal tip 21 of the catheter shaft 20 in the distal direction, the proportional support mechanism 135 moves proportional to this displacement and continuously supports the catheter shaft 20 at a point(s) between the center gear 80 and the distal end 16 of the housing 12 to prevent the catheter shaft 20 from buckling and/or kinking. In a preferred arrangement, the proportional support mechanism 135 continuously supports the catheter shaft 20 at a midpoint between the center gear 80 and the distal housing end 16. However, other points along the catheter shaft 20 could be utilized without departing from the scope of the subject disclosure.

Figure 16:
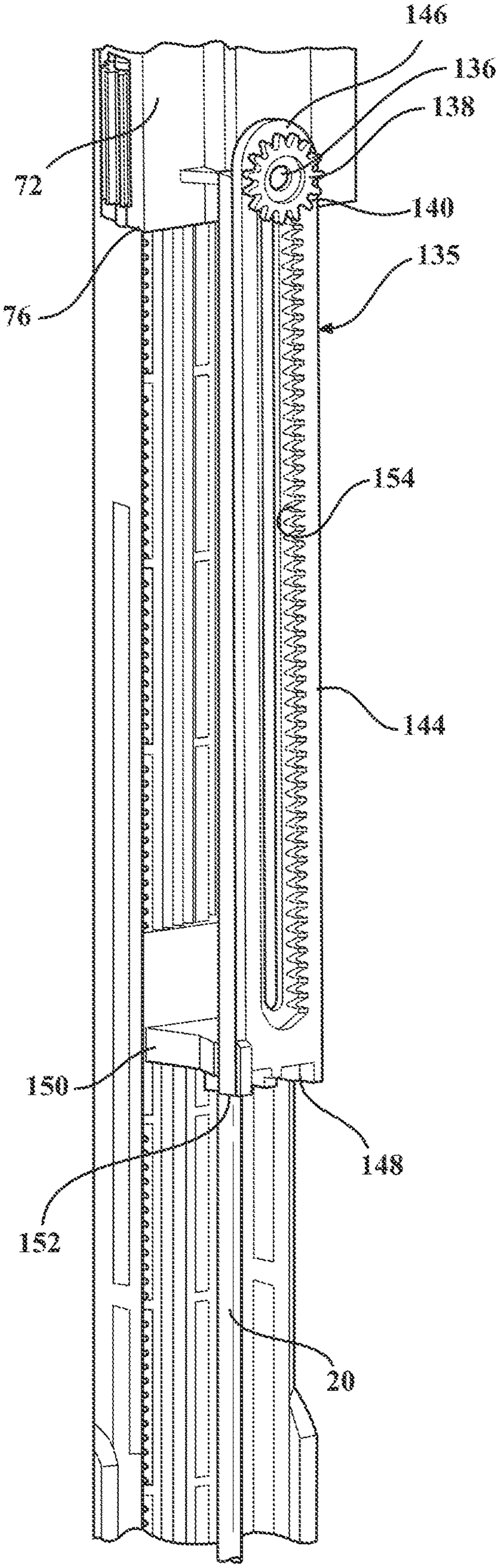
FIG. 16 is a perspective view of the proportional support mechanism illustrating a catheter support arm extending from a proximal support arm end operably coupled to a reduction gear to a distal support arm end, and a catheter support platform extending radially inwardly from the distal support arm end to define a catheter lumen for supporting the catheter shaft.
Figure 17:
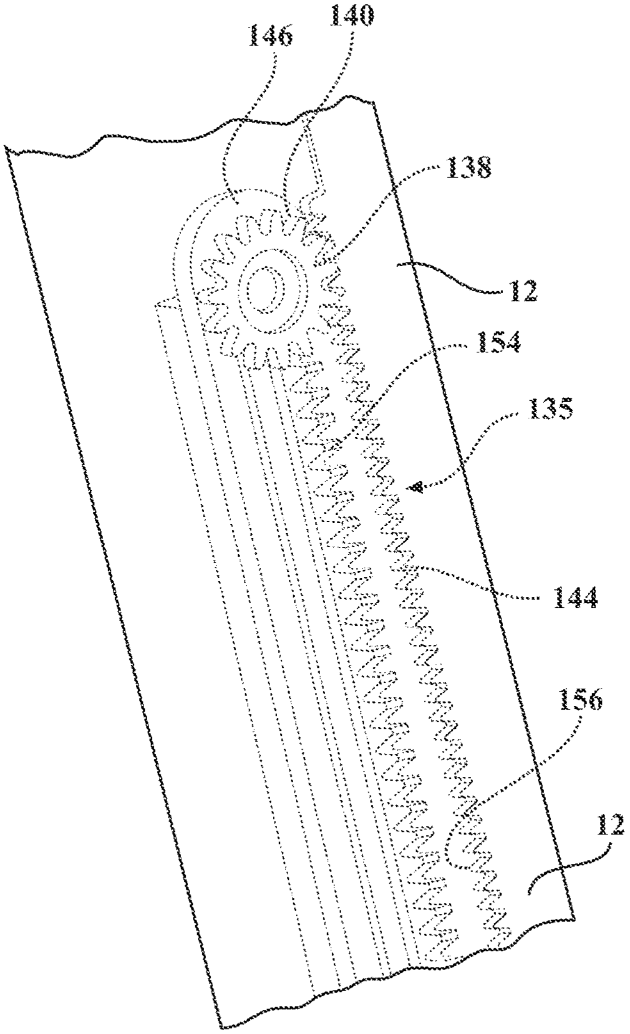
FIG. 17 is a transparent perspective view of a portion of the housing illustrating a minor gear rack of the catheter support arm operably coupled to a minor gear feature of the reduction gear and a major gear rack extending along the housing operably coupled to a major gear feature of the reduction gear.
Figure 18B:
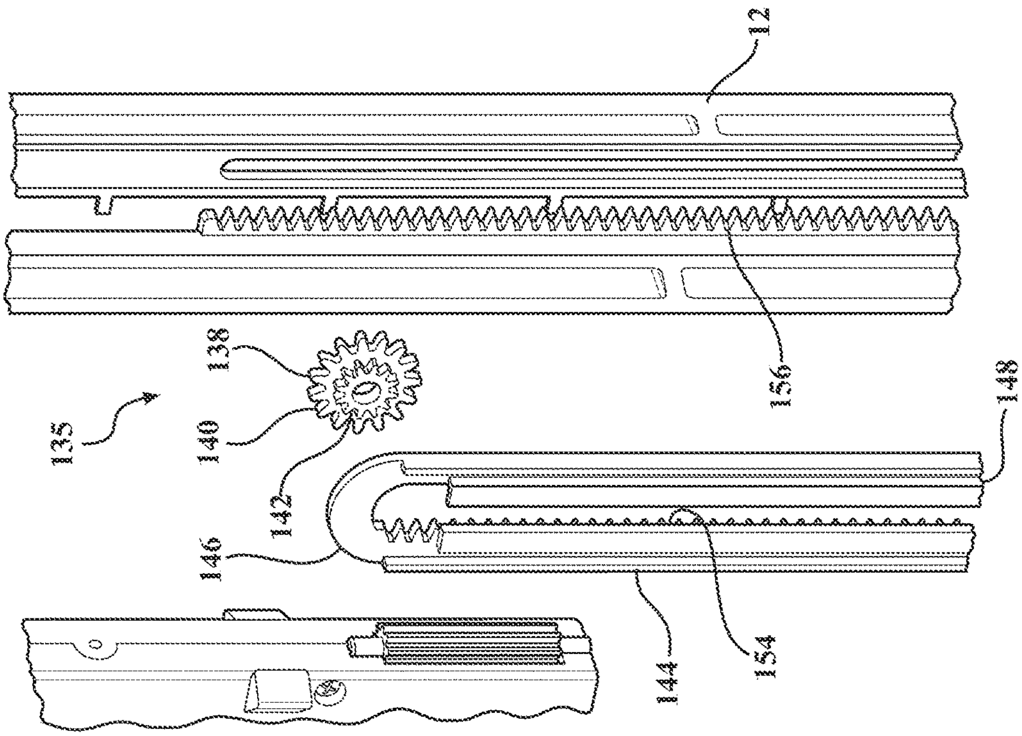
FIG. 18B is an exploded perspective view of the proportional support mechanism as viewed from a second opposite side of FIGS. 16 and 17 to more clearly illustrate the minor gear feature of the reduction gear for mating with the minor gear rack, and the major gear rack extending along the housing.
Figure 18A:
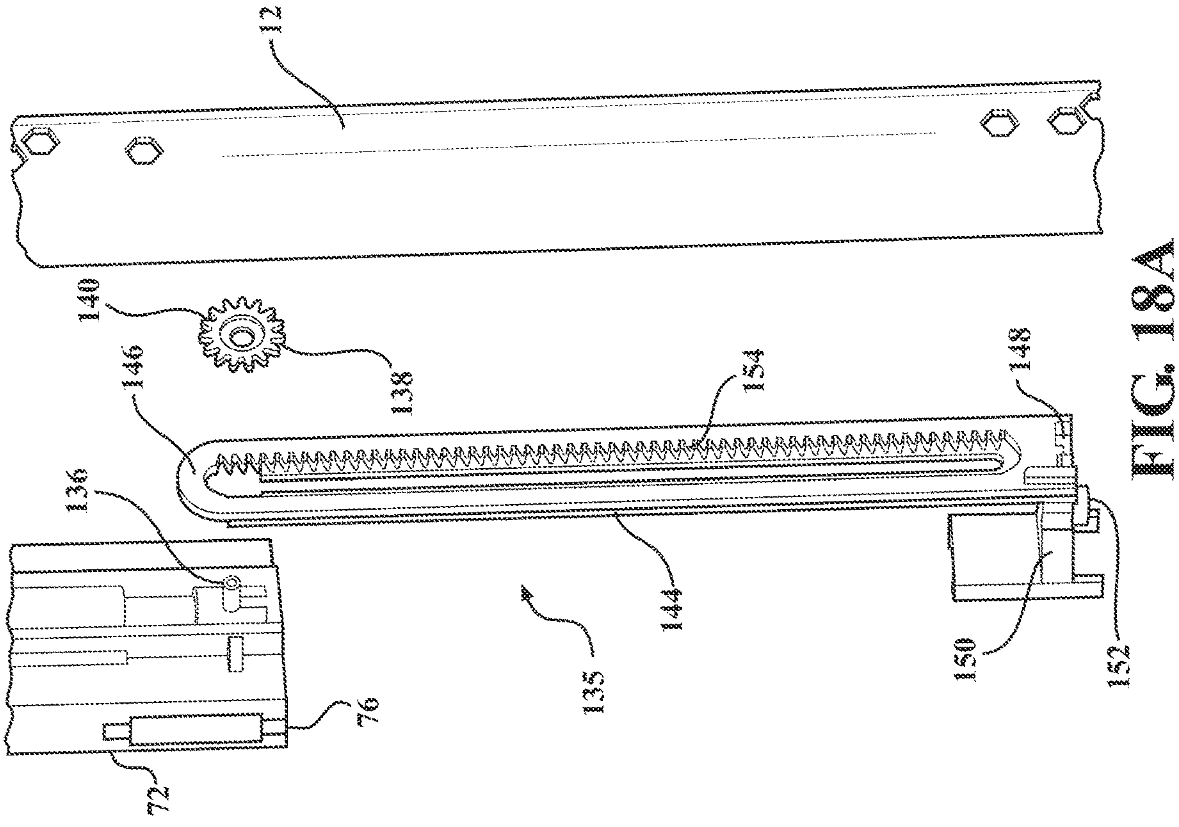
FIG. 18A is an exploded perspective view of the proportional support mechanism as viewed from a first side of FIGS. 16 and 17 to more clearly illustrate a gear boss extending from the distal case end and the minor gear rack extending between the catheter support arm between the proximal and distal support arm ends.

As best illustrated in FIGS. 16-18, the proportional support mechanism 135 includes a gear boss 136 extending radially outwardly from a distal case end 76 of the control case 72 and a reduction gear 138 having both a major gear feature 140 and a minor gear feature 142 is rotatably disposed on the gear boss 136. A catheter support arm 144 extends within the compartment 18 of the housing 12 from a first support arm end 146 operably coupled with the minor gear feature 142 of the reduction gear 138 to a second support arm end 148 disposed in spaced relationship with the distal end 16 of the housing 12. A catheter support platform 150 extends radially from the second support arm end 148 and defines a cathether lumen 152 through which the catheter shaft 20 passes as it extends between the center gear 80 and the distal end 16 of the housing 12. The catheter support arm 144 defines a minor gear rack 154 extending between the first and second support arm ends 146,148, and which is operably coupled with the minor gear feature of the reduction gear 138. The housing 12 also defines a major gear rack 156 operably coupled with the major gear feature 140 of the reduction gear 138. The major gear rack 156 extends from a starting position radially adjacent to the reduction gear 138 when the control case 72 is disposed adjacent the proximal housing end 14 to an ending position disposed adjacent the distal housing end 16.

In operation, since the reduction gear 138 is attached to an axle on the control case 72, namely the gear boss 136, linear manipulation of the control case 72 results in rotational engagement of the reduction gear 138 to its mating major and minor gear racks 154, 156. The ratio of translated linear motion between the major and minor gear racks 154,156 results in placement of the catheter support platform 150 of the catheter support arm 144 at a central position of the exposed catheter shaft 20. Put another way, with reference to FIGS. 15A-C, as the control case 72 is moved towards the distal housing end 16 of the housing 12, the reductive gear system provided by the reduction gear 138 and the major and minor gear racks 154, 156 maintains a distance between the catheter support platform 150 and the center gear 80 (Distance A) and a distance between the catheter support arm 150 and the distal housing end 16 of the housing 12 (Distance B) which are always equal. This is because the reduction gear system results in a reduced rate of axial movement of the catheter support arm 144 relative to the control case 72. In this way, the unsupported lengths of the shaft (Distances A and B) are always half that of the total unsupported length (A+B), promoting column strength by 2× and decreasing the effects of side loading that would otherwise induce buckling and kinking failures. It is understood that this mechanism may be duplicated within an embodiment of the catheter control assembly whereby a plurality of catheter support arms 144, each with their own reduction gears with specific minor and major gear diameters and associated racks, could be employed to support the catheter shaft at thirds, quarters, etc. in order to best minimize the risk of kinking and buckling over a given catheter length.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims.

What is claimed is:

1. A control assembly for a catheter having at least one working component, the control assembly comprising:

a housing extending along an axis between a proximal housing end and a distal housing end to define a housing compartment therebetween;

a control case disposed within said housing compartment adjacent said proximal housing end;

a catheter shaft extending within said housing compartment from said control case to a distal tip and rotatable about the axis during operation of the control assembly;

a fluid channel component and a working channel component of the catheter each extending from respective static portions disposed adjacent said proximal housing end in coupled and stationary relationship relative to said control case to respective dynamic portions extending along and rotatable about the axis simultaneously with said catheter shaft;

a lumen interruption mechanism disposed in said control case and extending from a proximal mechanism end disposed in communication with said static portions of said fluid and working channel components to a distal mechanism end disposed in communication with said dynamic portions of said fluid and working channel components for transitioning said fluid and working channel components from said respective static portions to said dynamic portions;

said lumen interruption mechanism including a cap fixed to said control case and disposed in a static condition relative to said housing and a hub rotatably coupled to said cap and rotatable about the axis;

said cap defining a central cap inlet extending along the axis and a cap fluid inlet disposed in radially offset relationship with said axis and extending in generally parallel relationship with said central cap inlet;

said central cap inlet coupled to said static portion of said working channel component and said cap fluid inlet coupled to said static portion of said fluid channel component;

said hub defining a central hub outlet extending along the axis and disposed in fluid communication with said central cap inlet and a hub fluid outlet disposed in radially offset relationship with said axis and in generally parallel relationship with said central cap outlet and in fluid communication with said cap fluid inlet; and said central hub outlet coupled to said dynamic portion of said working channel component and said hub fluid outlet coupled to said dynamic portion of said fluid channel component;

wherein said hub rotates simultaneously with both of said dynamic portions of said fluid and working channel components during rotation of said catheter shaft to maintain a position of said dynamic portions relative to one another and prevent kinking, winding and overlapping of said dynamic portions of said fluid and working channel components during simultaneous rotation with said catheter shaft.

2. The control assembly as set forth in claim 1, further comprising:

said hub defining a fluid reservoir extending circumferentially about said central hub outlet and disposed adjacent said cap and in continuous fluid communication with said cap fluid inlet during rotation of said hub relative to said cap;

said fluid reservoir disposed in fluid communication with said hub fluid outlet to establish a fluid communication path sequentially via said cap fluid inlet, said fluid reservoir and said hub fluid outlet; and at least one sealing device disposed between said hub and said cap to seal said fluid reservoir.

3. A control assembly for a catheter having at least one working component, the control assembly comprising:

a housing extending along an axis between a proximal housing end and a distal housing end to define a housing compartment therebetween;

a control case disposed within said housing compartment adjacent said proximal housing end;

a catheter shaft extending within said housing compartment from said control case to a distal tip and rotatable about the axis during operation of the control assembly;

at least one channel component of the catheter extending from a static portion disposed adjacent said proximal housing end in coupled and stationary relationship relative to said control case to a dynamic portion extending along and rotatable about the axis simultaneously with said catheter shaft;

a lumen interruption mechanism disposed in said control case and extending from a proximal mechanism end disposed in communication with said static portion of said at least one channel component to a distal mechanism end disposed in communication with said dynamic portion of said at least one channel component for transitioning said at least one channel component from said static portion to said dynamic portion;

said lumen interruption mechanism includes a cap fixed to said control case and disposed in a static condition relative to said housing and a hub rotatably coupled to said cap and rotatable about the axis;

said cap defining at least one cap inlet coupled with said static portion of said at least one channel component;

said hub defining at least one hub outlet disposed in communication with said at least one cap inlet and coupled with said dynamic portion of said at least one channel component;

wherein said hub rotates simultaneously with said dynamic portion of said at least one channel component during rotation of said catheter shaft to maintain a relative position of said dynamic portion relative to said catheter shaft and prevent kinking of said dynamic portion of said at least one channel component during rotation about the axis; and wherein said cap includes a post disposed in mating relationship with said control case to maintain said cap in said static position and a pair of legs extending along an outer portion of said hub and terminating in a rotational channel defined by said hub for establishing said rotatable coupling of said hub and cap.

4. A control assembly for a catheter having at least one working component, the control assembly comprising:

a housing extending along an axis between a proximal housing end and a distal housing end to define a housing compartment therebetween;

a control case disposed within said housing compartment adjacent said proximal housing end;

a catheter shaft extending within said housing compartment from said control case to a distal tip and rotatable about the axis during operation of the control assembly;

at least one channel component of the catheter extending from a static portion disposed adjacent said proximal housing end in coupled and stationary relationship relative to said control case to a dynamic portion extending along and rotatable about the axis simultaneously with said catheter shaft;

a lumen interruption mechanism disposed in said control case and extending from a proximal mechanism end disposed in communication with said static portion of said at least one channel component to a distal mechanism end disposed in communication with said dynamic portion of said at least one channel component for transitioning said at least one channel component from said static portion to said dynamic portion;

said lumen interruption mechanism includes a cap fixed to said control case and disposed in a static condition relative to said housing and a hub rotatably coupled to said cap and rotatable about the axis;

said cap defining at least one cap inlet coupled with said static portion of said at least one channel component;

said hub defining at least one hub outlet disposed in communication with said at least one cap inlet and coupled with said dynamic portion of said at least one channel component;

wherein said hub rotates simultaneously with said dynamic portion of said at least one channel component during rotation of said catheter shaft to maintain a relative position of said dynamic portion relative to said catheter shaft and prevent kinking of said dynamic portion of said at least one channel component during rotation about the axis;

said control case extending from a proximal case end to a distal case end to define a control compartment extending therebetween;

said lumen interruption mechanism disposed within said control compartment adjacent said proximal case end;

a center gear disposed in said control compartment adjacent said distal case end and coupled to said catheter shaft for driving simultaneous rotation therewith;

said center gear defining a set of center gear teeth extending radially outwardly from said center gear in circumferentially aligned relationship with the axis;

a rotation control knob rotatably disposed about said distal case end and operably coupled with said set of center gear teeth for driving rotation of said center gear and said catheter shaft in response to rotation of said rotation control knob by a user; and a synchronous rotation mechanism disposed in operably coupled relationship with said hub of said lumen interruption mechanism and said center gear to synchronously drive rotation of said hub in response to rotation of said center gear via said rotation control knob.

5. The control assembly as set forth in claim 4, further comprising:

said synchronous rotation mechanism including an axle extending from a proximal axle end operably coupled with said hub to a distal axle end operably coupled with said center gear, said axle rotatable in response to rotation of said center gear to establish said synchronous rotation of said hub.

6. The control assembly as set forth in claim 5, further comprising:

said axle extending within said control compartment in aligned relationship with said axis, and said proximal axle end directly connected to said hub and said distal axle end directly connected to said center gear to establish said synchronous rotation of said hub and said center gear.

7. The control assembly as set forth in claim 6, wherein said axle defines an internal passageway extending within said axle between said proximal and distal ends;

and said dynamic portion of said at least one channel component extending from said at least one hub outlet, through said internal passageway and into said catheter shaft.

8. The control assembly as set forth in claim 4, further comprising:

a cable take-up assembly disposed in said control compartment of said control case and rotatable about the axis synchronously with said hub and said center gear;

said cable take-up assembly defining a spool extending circumferentially about the axis;

an electronics cable of the catheter extending from a static cable portion to a dynamic cable portion extending along and rotatable simultaneously about the axis with said catheter shaft; and said electronics cable routed to said spool of said cable take-up assembly between said static and dynamic cable portions;

wherein synchronous rotation of said cable take-up assembly with said hub and said center gear in a first rotational direction winds said electronics cable around said spool and synchronous rotation of said cable take-up assembly with said hub and said center gear in a second opposite rotational direction unwinds said electronics cable from said spool for allowing said dynamic portion of said electronics cable to maintain a position relative to said dynamic portion of said at least one channel component during simultaneous rotation with said catheter shaft.

9. The control assembly as set forth in claim 8, wherein said cable take-up assembly is disposed on said center gear.

10. The control assembly as set forth in claim 8, wherein said cable take-up assembly is disposed on said lumen interruption mechanism.

11. The control assembly as set forth in claim 8, wherein said electronics cable is routed through a tensioning mechanism prior to said spool to continuously apply a tension to said electronics cable during rotation of said spool in both the first and second rotational directions and maintain the portion of said electronics cable routed around said spool taught during operation of said cable take-up assembly.

12. The control assembly as set forth in claim 4, further comprising:

said center gear defining a center gear passageway extending along the axis;

an anchor arm disposed within said control compartment adjacent said center gear and rotatable about the axis;

said anchor arm having an anchor shaft extending axially into said center gear passageway;

at least one pull wire extending from said anchor arm to said distal tip of said catheter shaft for use in deflecting said distal tip;

said center gear defining at least one axial slot extending radially outwardly from said center gear passageway; and said anchor shaft including at least one axial rib extending radially outwardly in aligned and radially spaced relationship with the axis and disposed in mating relationship with said at least one axial slot to drive synchronous rotation of said anchor arm about the axis in response to rotation of said center gear for maintaining a radial orientation of said at least one pull wire relative to said catheter shaft.

13. The control assembly as set forth in claim 12, further comprising:

said anchor arm defining a circumferential slot extending radially inwardly from an anchor passageway extending through said anchor arm and said anchor shaft along the axis;

a lead screw disposed within said control compartment adjacent said anchor arm;

said lead screw including a rotor flange coupled with said circumferential slot to allow rotation of said anchor arm relative to said lead screw during rotation of said center gear;

a threaded gear disposed within the control compartment in threaded relationship with said lead screw; and a deflection control knob rotatably disposed about said proximal case end of said control case and in operably coupled relationship with said threaded gear;

wherein rotation of said deflection control knob in a first rotational direction ultimately drives said threaded gear to axially displace said lead screw relative to said threaded gear in a proximal direction, and wherein said axial displacement of said lead screw in said proximal direction pulls said anchor arm relative to said center gear and slides said at least one axial rib within said at least one axial slot via said coupling of said rotor flange of said anchor arm and said circumferential slot to apply a resultant tension on said at least one pull wire and deflect said distal tip of said catheter shaft.

14. The control assembly as set forth in claim 13, further comprising at least one deflection spur gear arranged in radially offset relationship to said threaded gear and disposed in operably coupled relationship between said threaded gear and said deflection control knob.

15. The control assembly as set forth in claim 13, wherein said control case defines a wing slot disposed adjacent said lead screw, and wherein said lead screw includes an anti-torque wing extending radially outwardly and disposed in mating relationship with said wing slot to prevent said lead screw from rotating about said axis and limit movement of said lead screw to said proximal direction during said axial movement of said lead screw via said threaded gear.

16. The control assembly as set forth in claim 4, further comprising:

said control case axially translatable along said housing from said proximal housing end towards said distal housing end to axially advance said catheter shaft along the axis and exit said distal tip out of said distal housing end; and a proportional support mechanism disposed within the housing compartment and continuously supporting said catheter shaft at a point between said center gear and said distal housing end during said axial advancement of said catheter shaft to prevent said catheter shaft from bucking or kinking.

17. The control assembly as set forth in claim 16, wherein said proportion support mechanism continuously supports said catheter shaft at a midpoint between said center gear and said distal housing end during said axial advancement of said catheter shaft.

18. The control assembly as set forth in claim 17, further comprising:

said proportional support mechanism including a gear boss extending radially outwardly from said distal case end of said control case and a reduction gear having both a major gear feature and a minor gear feature rotatably disposed on said gear boss;

a catheter support arm extending within said housing compartment from a proximal support arm end to a distal support arm end disposed in spaced relationship with said distal housing end;

a catheter support platform extending radially from said distal support arm end and defining a catheter lumen supporting said catheter shaft at said midpoint between said center gear and said distal housing end;

said catheter support arm defining a minor gear rack operably coupled with said minor gear feature of said reduction gear and extending between said proximal and distal support arm ends; and said housing defining a major gear rack operably coupled with said major gear feature of said reduction gear;

wherein said reduction gear and said major and minor gear racks collectively and consistently maintain a distance A extending between said center gear and said catheter support arm being equal to a distance B extending between said catheter support arm and said distal housing end during said axially translation of said control case along said housing to establish said support of said catheter shaft by said catheter support arm at said midpoint between said center gear and said distal housing end.

* * * * *